United States Patent
Ikehashi et al.

(10) Patent No.: US 10,598,647 B2
(45) Date of Patent: Mar. 24, 2020

(54) GAS SENSOR AND MANUFACTURING METHOD OF THE SAME

(71) Applicant: KABUSHIKI KAISHA TOSHIBA, Tokyo (JP)

(72) Inventors: Tamio Ikehashi, Kanagawa (JP); Hiroaki Yamazaki, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 196 days.

(21) Appl. No.: 15/914,828

(22) Filed: Mar. 7, 2018

(65) Prior Publication Data

US 2019/0086377 A1 Mar. 21, 2019

(30) Foreign Application Priority Data

Sep. 20, 2017 (JP) .................... 2017-180740

(51) Int. Cl.
*G01N 33/00* (2006.01)
*G01N 27/22* (2006.01)
*G01N 25/20* (2006.01)

(52) U.S. Cl.
CPC ........ *G01N 33/0022* (2013.01); *G01N 25/20* (2013.01); *G01N 27/221* (2013.01); *G01N 27/227* (2013.01); *G01N 33/005* (2013.01); *G01N 2027/222* (2013.01)

(58) Field of Classification Search
USPC ...................................................... 73/31.06
See application file for complete search history.

(56) References Cited

U.S. PATENT DOCUMENTS

| | | | | |
|---|---|---|---|---|
| 7,038,470 B1 * | 5/2006 | Johnson | ............... | G01N 27/226 250/390.05 |
| 8,921,958 B2 * | 12/2014 | Ikehashi | ............... | B81B 3/0018 257/254 |
| 9,038,437 B2 * | 5/2015 | Offermans | ......... | G01N 33/0009 73/31.06 |

(Continued)

FOREIGN PATENT DOCUMENTS

| | | |
|---|---|---|
| EP | 2 169 400 A1 | 3/2010 |
| JP | 2014-228447 | 12/2004 |

(Continued)

OTHER PUBLICATIONS

J.F. Creemer et al., "Microhotplates with TiNheaters," Sensors and Actuators A: Physical (vol. 148, No. 2) Sep. 3, 2008, pp. 1-6 (416-421).

(Continued)

*Primary Examiner* — Clayton E. LaBalle
*Assistant Examiner* — Warren K Fenwick
(74) *Attorney, Agent, or Firm* — Finnegan, Henderson, Farabow, Garrett & Dunner, L.L.P.

(57) ABSTRACT

According to one embodiment, a gas sensor is disclosed. The gas sensor includes a substrate region, a first electrode provided on the substrate region, and a movable structure above the first electrode. The movable structure includes a deformable member which deforms by absorbing or adsorbing a predetermined gas, a heat member which heats the deformable member, and a second electrode. The gas sensor further includes a first cavity region which is provided between the first electrode and the second electrode.

20 Claims, 28 Drawing Sheets

(56) References Cited

U.S. PATENT DOCUMENTS

| | | | |
|---|---|---|---|
| 9,274,017 B2* | 3/2016 | Nakamura | G01L 9/0072 |
| 9,417,202 B2* | 8/2016 | Park | G01N 27/12 |
| 2014/0338459 A1* | 11/2014 | Besling | G01L 9/0073 |
| | | | 73/718 |
| 2016/0103082 A1 | 4/2016 | Kimura | |
| 2016/0187370 A1* | 6/2016 | Ikehashi | G01P 15/125 |
| | | | 73/514.32 |
| 2017/0057811 A1* | 3/2017 | Shimooka | B81B 7/0038 |
| 2017/0343522 A1 | 11/2017 | Ikehashi et al. | |

FOREIGN PATENT DOCUMENTS

| | | |
|---|---|---|
| JP | 2012/230071 | 11/2012 |
| JP | 2016-170161 | 9/2016 |
| JP | 2017-215170 | 12/2017 |

OTHER PUBLICATIONS

Sadaki Nakano et al., "Hydrogen Gas Detection System Prototype with Wireless Sensor Networks," IEEE Sensors 2005 (The 4$^{th}$ IEEE Conference on Sensors), Oct. 30-Nov. 3, 2005, pp. 159-162.

Baselt et al., "Design and performance of a microcantilever-based hydrogen sensor," Sensors and Actuators B 88, pp. 120-131 (2003).

Yamazaki et al.; "A High Sensitivity MEMS Capacitive Hydrogen Sensor With Inverted T-Shaped Electrode and Ring-Shaped Palladium," Transducers 2017, Kaohsiung, Taiwan, pp. 226-229 (Jun. 18-22, 2017).

\* cited by examiner

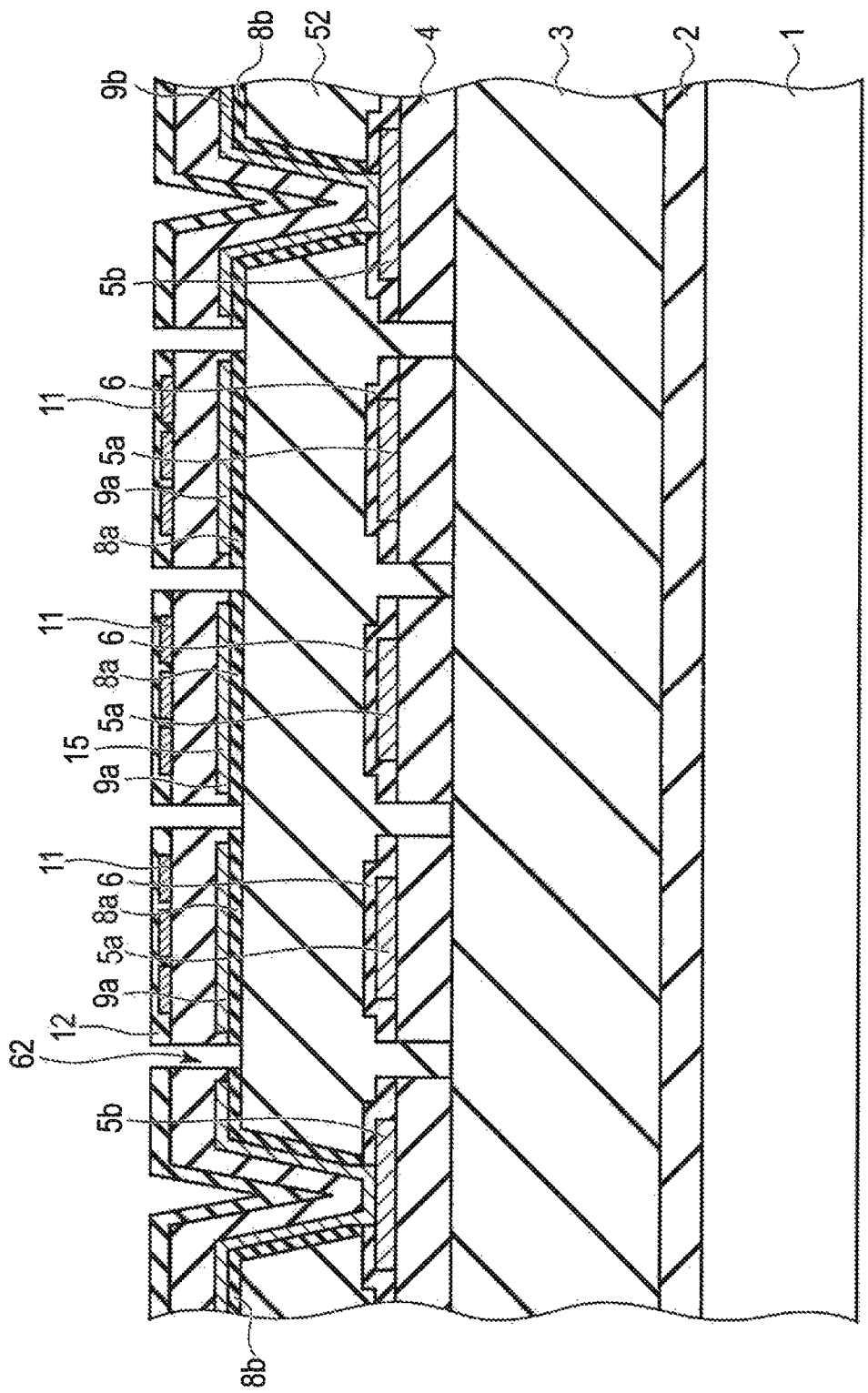
F I G. 15

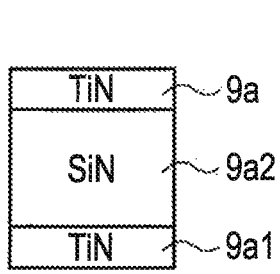
F I G. 21A
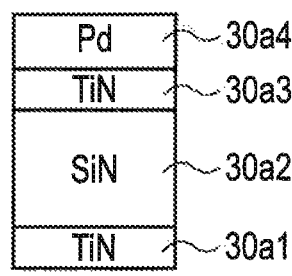
F I G. 21B
F I G. 21C
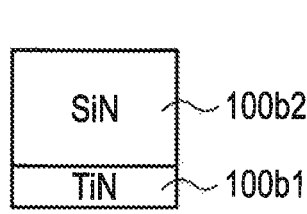
F I G. 21D
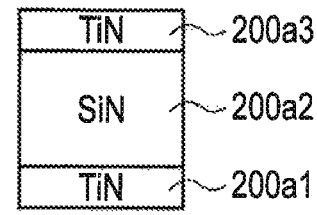
F I G. 21E

GAS SENSOR AND MANUFACTURING METHOD OF THE SAME

CROSS-REFERENCE TO RELATED APPLICATIONS

This application is based upon and claims the benefit of priority from Japanese Patent Application No. 2017-180740, filed Sep. 20, 2017, the entire contents of which are incorporated herein by reference.

FIELD

Embodiments described herein relate generally to a gas sensor and manufacturing method of the same.

BACKGROUND

It is proposed gas sensors that sense gas such as hydrogen gas, and are formed by using micro-electromechanical systems (MEMS) technique. However, it is not necessarily said that a gas sensor having sufficient performance is proposed.

BRIEF DESCRIPTION OF THE DRAWINGS

FIG. 15 is a cross-sectional view for explaining the manufacturing method of the hydrogen sensor according to the first embodiment continued from FIG. 14.

FIGS. 21A, 21B, 21C, 21D and 21E are cross-sectional views for explaining specific materials for elements constituting the hydrogen sensor according to the third embodiment.

DETAILED DESCRIPTION

Figure 1:
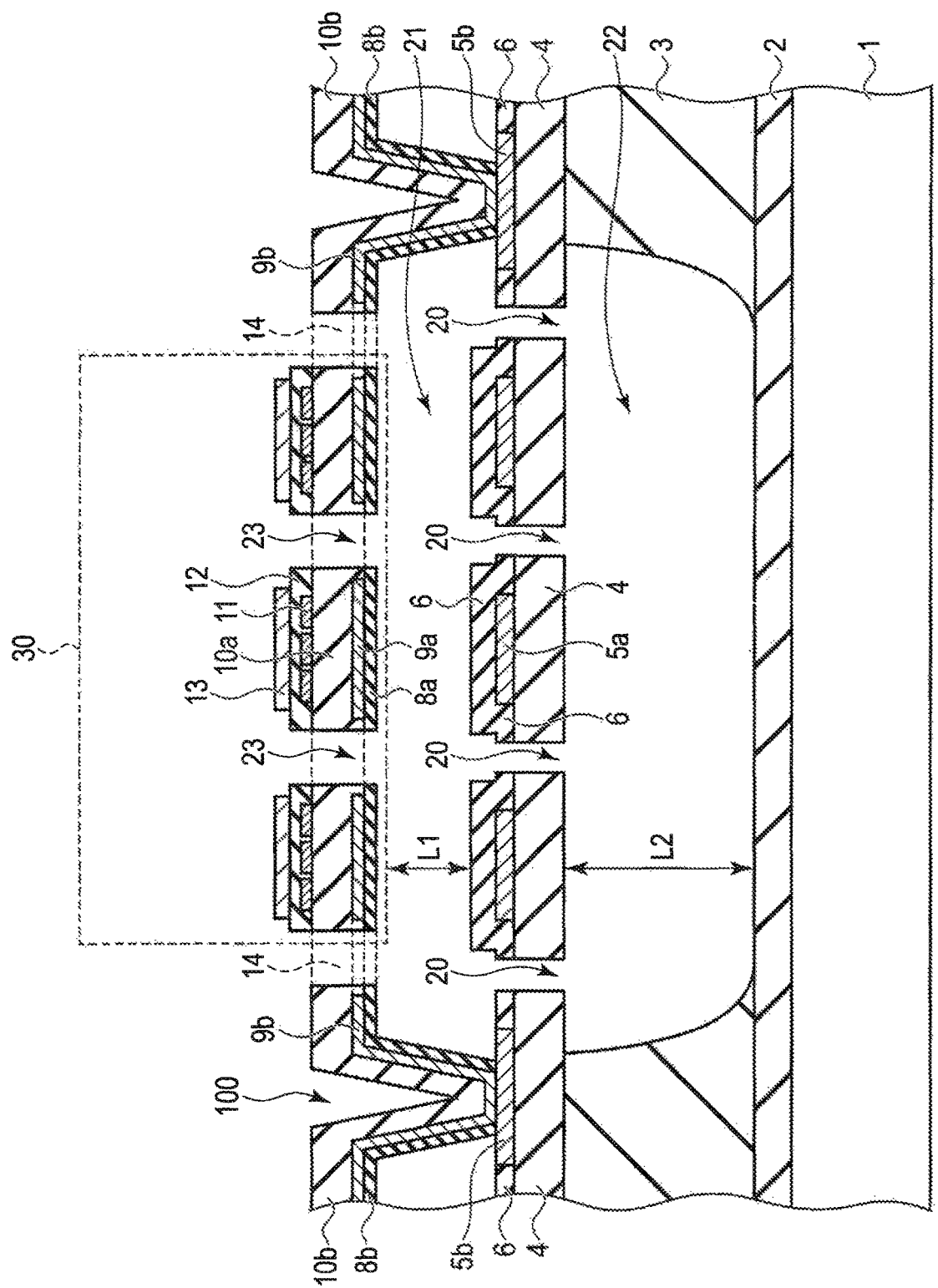
FIG. 1 is a cross-sectional view schematically showing a hydrogen sensor according to a first embodiment.

In general, according to one embodiment, a gas sensor is disclosed. The gas sensor includes a substrate region. A first electrode is provided on the substrate region. A movable structure is provided above the first electrode. The movable structure includes a deformable member configured to deform by absorbing or adsorbing a predetermined gas, a heating member configured to heat the deformable member, and a second electrode. A first cavity region is provided between the first electrode and the second electrode.

According to another embodiment, a manufacturing method of a gas sensor is disclosed. A first insulating layer, a second insulating layer, and a first electrode are formed in sequence on a semiconductor substrate. A third insulating layer is formed on the second insulating layer and the first electrode. A through hole is formed, which penetrates the third insulating layer and the second insulating layer, and reaches the first insulating layer is formed. A fourth insulating layer is formed on the first insulating layer and the third insulating layer to fill the through hole with the fourth insulating layer. A movable structure is formed on the fourth insulating layer. The movable structure includes a deformable member configured to deform by absorbing or adsorbing a predetermined gas, a heating member configured to heat the deformable member, and a second electrode. A first cavity region is formed between the first electrode and the second electrode, by removing the fourth insulating layer.

Embodiments will be described hereinafter with reference to the accompanying drawings. The drawings are schematic or conceptual drawings, and dimensions and ratios are not necessarily the same as those in reality. Further, in the drawings, the same reference symbols (including those having different subscripts) denote the same or corresponding parts, and overlapping explanations thereof will be made as necessary. In addition, as used in the description and the appended claims, what is expressed by a singular form shall include the meaning of "more than one."

First Embodiment

Figure 2A:
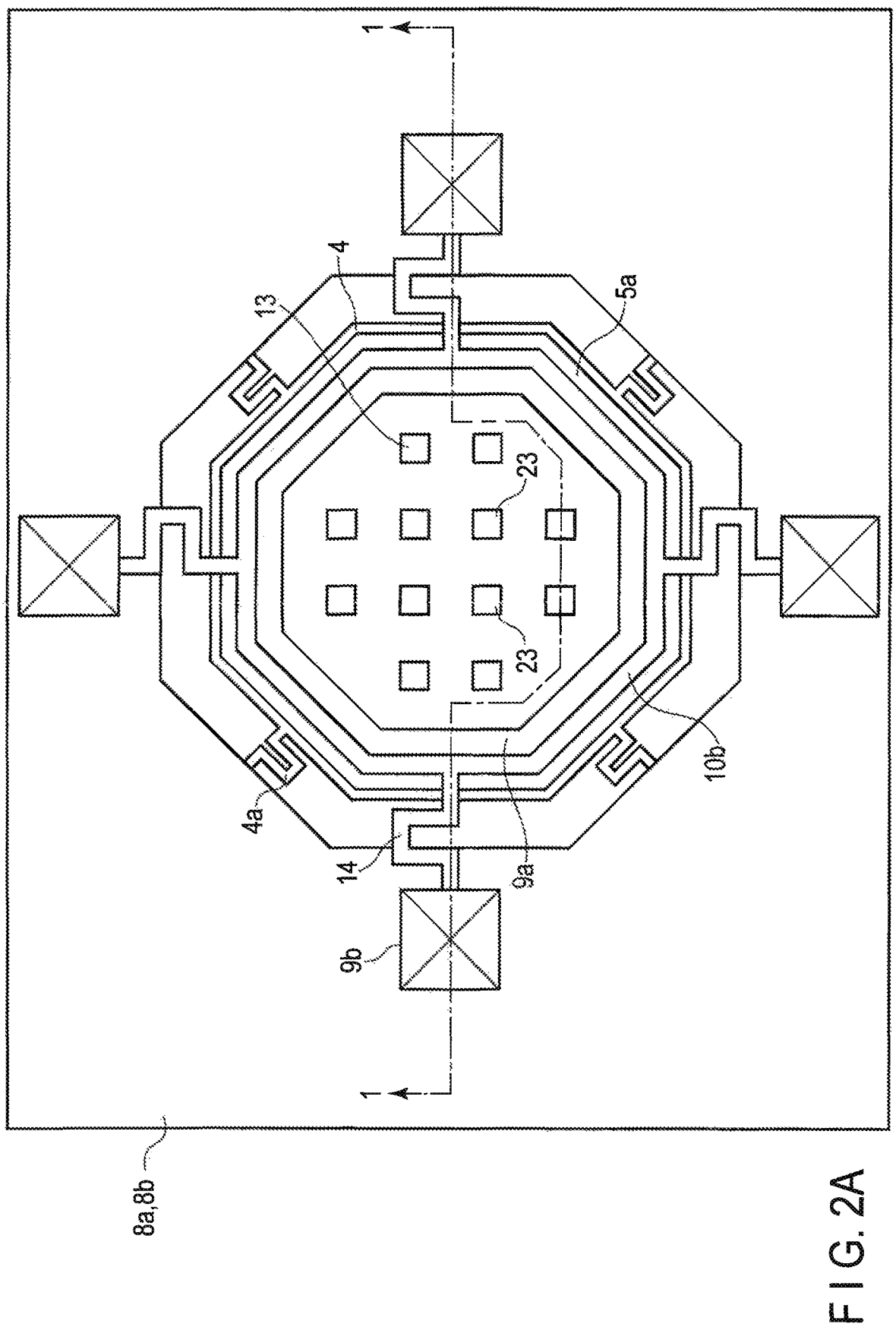
FIG. 2A is a plan view schematically showing the hydrogen sensor according to the first embodiment.
Figure 2B:
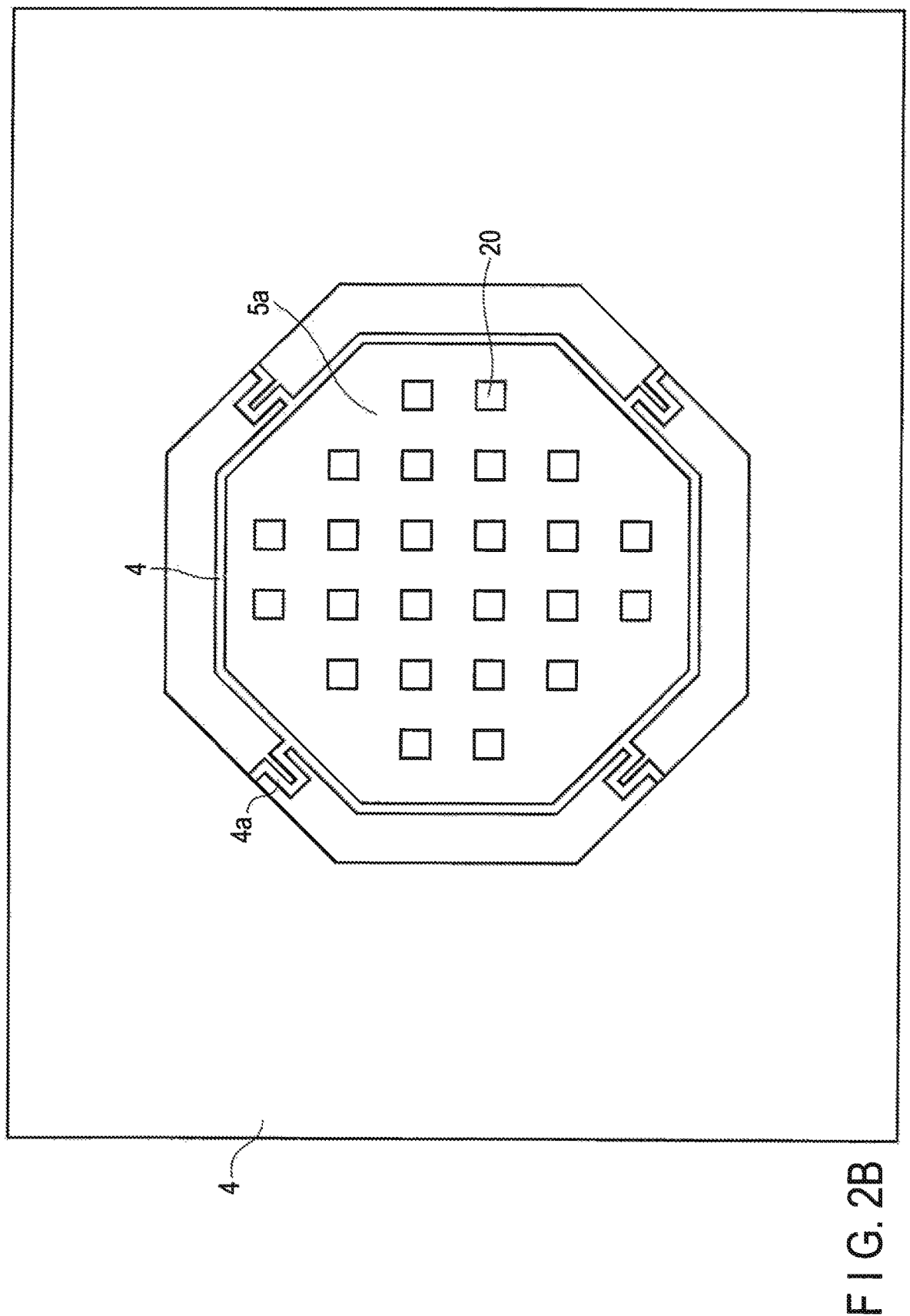
FIG. 2B is a plan view schematically showing a region including an upper electrode of the hydrogen sensor according to the first embodiment.
Figure 2C:
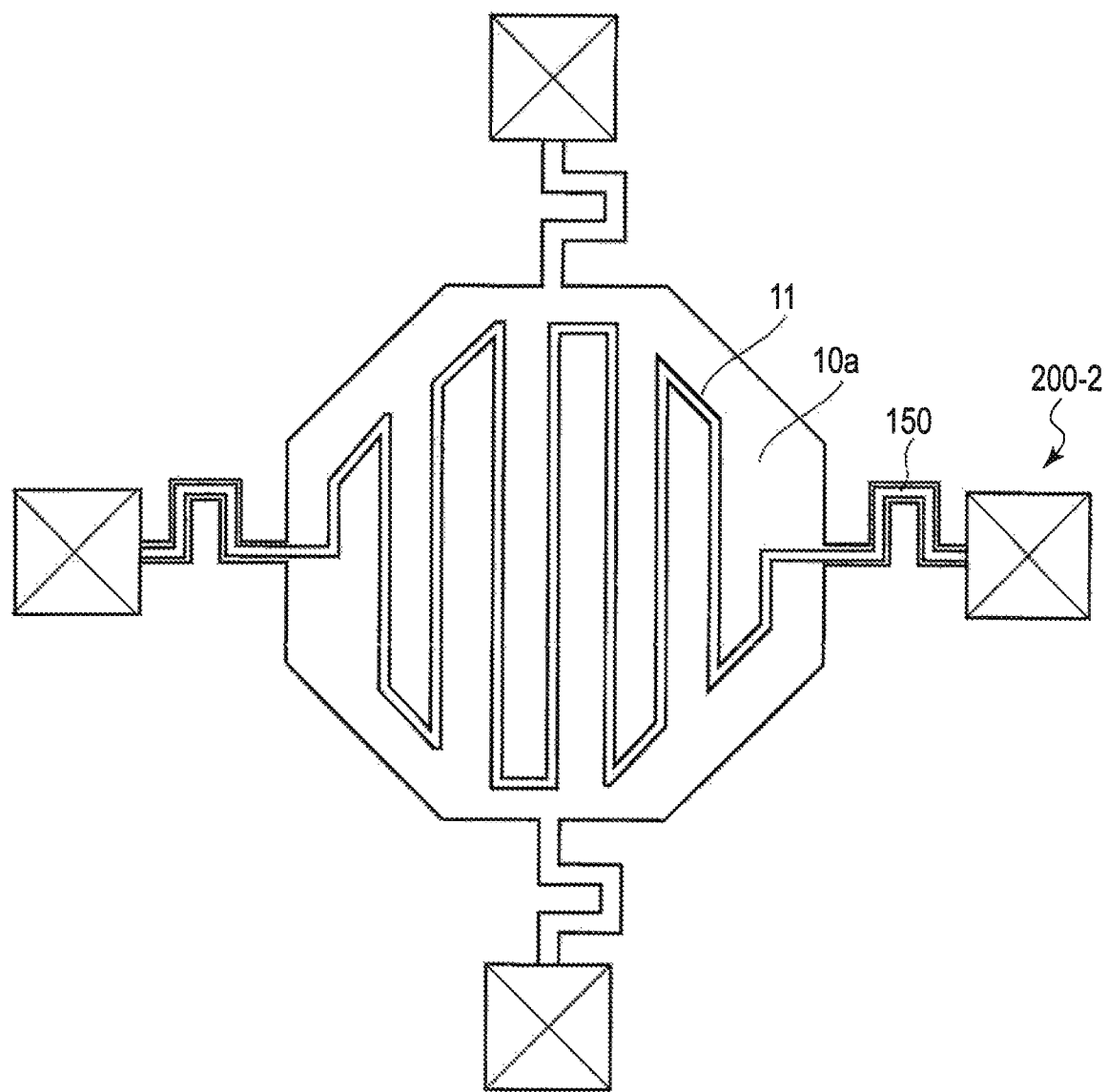
FIG. 2C is a plan view schematically showing a region including a heater of the hydrogen sensor according to the first embodiment.

FIG. 1 is a cross-sectional view schematically showing a hydrogen sensor according to a first embodiment. FIG. 2A is a plan view schematically showing the hydrogen sensor according to the present embodiment. The cross-sectional view of FIG. 1 corresponds a cross-sectional view along line 1-1 of the plan view of FIG. 2A. FIG. 2B is a plan view schematically showing a region including an upper electrode 9a of the hydrogen sensor according to the present embodiment. FIG. 2C is a plan view schematically showing a region including a heater 11 of the hydrogen sensor according to the present embodiment. The hydrogen sensor according to the present embodiment is a capacitance type hydrogen sensor utilizing a MEMS capacitor, and is configured to sense gaseous hydrogen.

In FIG. 1, a reference symbol 1 denotes a silicon substrate (substrate region), and an insulating layer (substrate region) 2 and an insulating layer 3 (substrate region) are provided in sequence on the silicon substrate 1. It is acceptable to use a semiconductor substrate other than the silicon substrate.

A material for the insulating layer 2 differs from a material for the insulating layer 3. For example, when the insulating layer 2 and insulating layer 3 are subjected to ashing (dry etching) by using oxygen ($O_2$), the materials for the insulating layer 2 and in layer 3 are selected in such a manner that an etching rate of the insulating layer 3 becomes higher than an etching rate of the insulating layer 2. The material for the insulating layer 2 is, for example, silicon nitride, and material for the insulating layer 3 is, for example, a polyimide. The insulating layer 3 is thicker than, for example, the insulating layer 2.

The insulating layer 3 is provided with an opening extending to the insulating layer 2, and part of an upper surface of the insulating layer 2 is exposed. In the present embodiment, as shown in the cross-sectional view of FIG. 1, a side surface of the insulating layer 3 has a tapered shape (downward convex curve) with a width that decreases from top toward down with respect to a surface of the silicon substrate 1. The cross section of the side surface of the insulating layer 3 may be defined by straight lines, or furthermore, may be defined by straight lines and curved lines. Furthermore, the side surface of the insulating layer 3 defining the opening becomes a curved surface in Cartesian coordinate system defined by three axes that are mutually-perpendicular. The curved surface has, for example, a negative curvature.

An insulating layer 4 is provided on the insulating layer 3 to straddle the opening. The insulating layer does not infill the opening. As a result, a cavity region (second cavity region) 22 is defined by the insulating layer 3 and insulating layer 4. A height (dimension) L2 of the cavity region 22 is greater than, for example, 10 μm. The insulating layer 4 and an insulating layer 6 are provided with spring sections 4a for the lower electrode (FIG. 2A). A material for the insulating layer 4 is, for example, silicon nitride.

An lower electrode 5a, and a metal layer 5b for electrical conductor are provided on the insulating layer 4.

The lower electrode 5a and metallic layer 5b contain an identical electrical conducting material such as aluminum (Al), titanium (Ti) or titanium nitride (TiN).

An insulating layer 6 is provided on the lower electrode 5a and insulating layer 4. A material for the insulating layer 6 is, for example, silicon nitride.

A movable structure 30 is located above the lower electrode 5a, and a position of the movable structure 30 changes upward or downward in accordance with a change in hydrogen concentrations. The movable structure 30 includes a structure in which an insulating layer 8a, an upper electrode 9a, an insulating layer 10a, a heater 11, an insulating layer 12, and a hydrogen occlusion layer 13 are stacked in sequence.

A cavity region (first cavity region) 21 is provided between the lower electrode 5a and upper electrode 9a, and is defined by the insulating layers 6 and 8a between the lower electrode 5a and upper electrode 9a. A height (dimension) L1 of the cavity region 21 is, for example, 2 to 3 μm. L2 and L1 are determined to satisfy the magnitude relationship of L2>L1. Through holes 20 connected with the cavity region 21 and cavity region 22 are provided in the insulation layers 4 and 6.

The upper electrode 9a is provided on the insulating layer 8a to face the lower electrode 5a. A material for the upper electrode 9a contains, for example, TiN. Other electrical conducting material such as Ti may be used instead of TiN.

The insulating layer 10a covers an upper surface and side surfaces of the upper electrode 9a. A material for the insulating layer 10a contains, for example, silicon nitride.

The heater 11 is provided on the upper surface of the insulating layer 10a. A material for the heater 11 contains, for example, TiN. The material for the heater 11 and the material for the upper electrode 9a may be identical to each other or may be different from each other. For example, the heater 11 employs resistance heating as a heat generating means, and is constituted using a material such as Ti, Ni, Cu, Pd, Pt, or Pd—Ni.

An insulating layer 12 is provided on the insulating layer 10a and heater 11, and configured to cover the heater 11. Through holes 23 connected with the cavity region 21 are provided in the insulating layers 8a, 10a, and 12.

The hydrogen occlusion layer 13 is provided on the insulating layer 12. A material for the hydrogen occlusion layer 13 contains, for example, palladium (Pd), an alloy containing palladium, an alloy containing palladium in which cupper (Cu) and silicon (Si) are contained, an alloy containing titanium (Ti), an alloy containing lantern (La), or metallic glass. The metallic glass contains, for example, the aforementioned metal (Pd, Ti or La) or an alloy of the metals.

The hydrogen occlusion layer 13 expands (increases volume thereof) by absorbing or adsorbing (accumulating) hydrogen. When the hydrogen occlusion layer 13 expands, the movable structure 30 is deformed, and thus a distance between the lower electrode 5a and upper electrode 9a is changed.

The amount of expansion of the hydrogen occlusion layer 13 changes according to the amount of hydrogen absorption or amount of hydrogen adsorption, so that the distance between the lower electrode 5a and upper electrode 9a changes according to the amount of hydrogen absorption or the amount of hydrogen adsorption. As a result, the capacitance of the MEMS capacitor changes according to the amount of hydrogen absorption or amount of hydrogen adsorption of the hydrogen occlusion layer 13. Accordingly, the hydrogen concentrations around the hydrogen occlusion layer 13 can be calculated by obtaining the capacitance of the MEMS capacitor. The capacitance is calculated by, for example, a well-known detecting circuit (not shown) formed in the silicon substrate 1. The detecting circuit is formed by using, for example, a CMOS circuit. The detecting circuit may be formed in a silicon substrate (semiconductor substrate) separate from the silicon substrate 1 or may be formed in a chip separate from the chip formed by using the silicon substrate 1. Furthermore, the detecting circuit may be an external circuit externally that is attachable to the silicon substrate 1.

Each of both ends of the movable structure 30 is connected to an anchor 9b provided on the insulating layer 4 through the spring section 14. An insulating layer 8b is provided on the under side of the anchor 9b, and insulating layer 10b is provided on the upper side of the anchor 9b.

The hydrogen sensor according to the present embodiment is configured such that the hydrogen occlusion layer 13 can be heated by the heater 11. Humidity or the like around the hydrogen occlusion layer 13 serves as a disturbance that influences the detection accuracy. Thus, in the present embodiment, the hydrogen occlusion layer 13 is heated by the heater 11 to maintain the humidity or the like in a constant level, thereby reducing the influence of the disturbance. Further, heating the hydrogen occlusion layer 13 contributes to the improvement of responsiveness and hysteresis of the sensor. The hydrogen occlusion layer 13 is heated by heater 11, for example, before performing the detection of hydrogen. The hydrogen occlusion layer 13 is not necessarily heated each time before performing the detection of hydrogen. The hydrogen occlusion layer 13 may be heated each time a predetermined number of times of the hydrogen detection is carried out.

In order to suppress increasing of power consumption of the heater 11, heat loss from the movable structure 30 should be reduced. For that purpose, for example, the first cavity region 21 under the movable structure 30 is enlarged to increase thermal resistance thereof. Enlarging the first cavity region requires increasing the distance between the lower electrode 5a and the upper electrode 9a. Increasing the distance causes capacitance reduction of the HEMS capacitor. As a result, the detection sensitivity of the hydrogen concentrations is lowered.

Thus, in the present embodiment, the second cavity region 22 connected with the first cavity region 21 is provided. The first cavity region 21 and the second cavity region 22 are connected in series. Accordingly, the total thermal resistance of the thermal resistance (Rtemp1) of the first cavity region 21 and thermal resistance (Rtemp2) of the second cavity region 22 is the sum of Rtemp1 and Rtemp2. Thereby enabling the thermal resistance of the cavity region under the movable structure 30 to increase, and thus the detection sensitivity is increased while the increasing of the power consumption of the heater 11 is suppressed. Therefore, according to the present embodiment, the hydrogen sensor having sufficient performance can be provided.

Hereinafter, the hydrogen sensor according to the present embodiment will further be described according to manufacturing steps of the hydrogen sensor.

FIG. 3 to FIG. 16 are cross-sectional views for explaining the manufacturing method of the hydrogen sensor according to the present embodiment.

Figure 3:
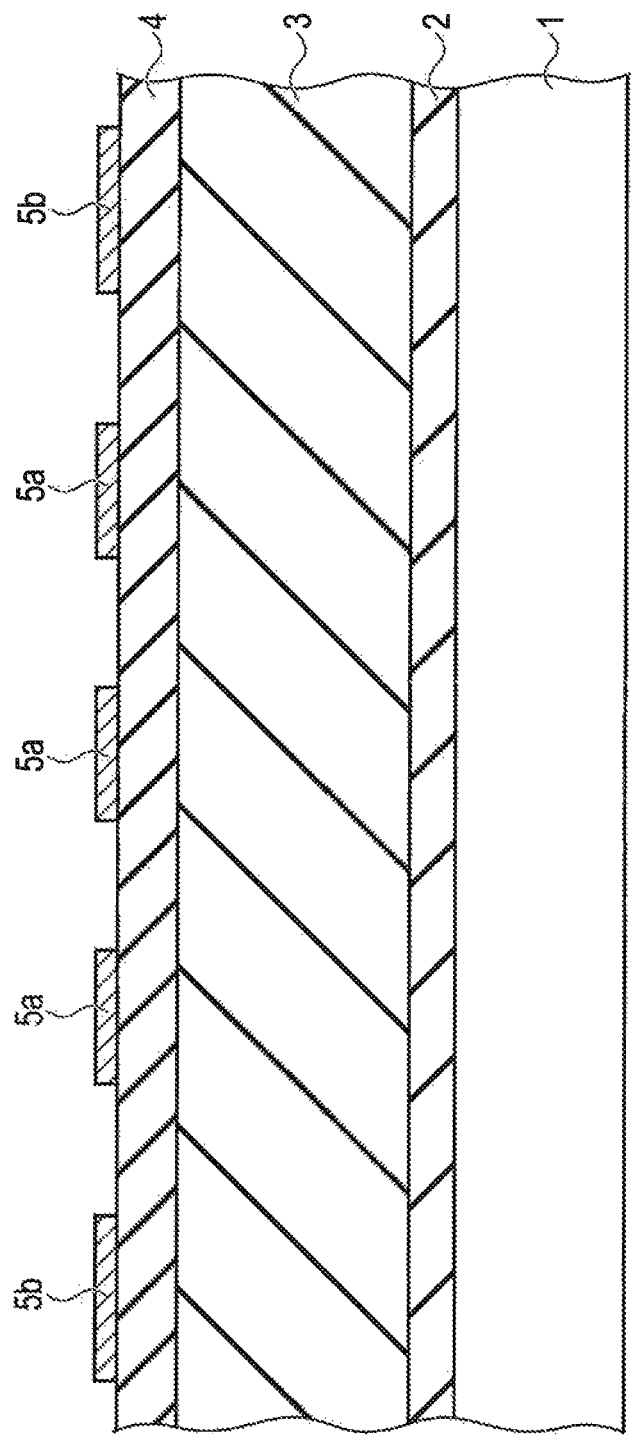
FIG. 3 is a cross-sectional view for explaining a manufacturing method of the hydrogen sensor according to the first embodiment.

First, as shown in FIG. 3, the insulating layer 2, the insulating layer 3 (first insulating layer), and the insulating layer 4 (second insulating layer) are formed in sequence on the silicon substrate 1. An electrical conducting layer to be processed into the lower electrode 5a and metallic layer 5b is formed on the insulating layer 4, a resist pattern (not shown) formed on the electrical conducting layer, and the electrical conducting layer is subjected to etching by using the resist pattern as a mask, whereby the lower electrode 5a and metallic layer 5b are formed.

Figure 4:
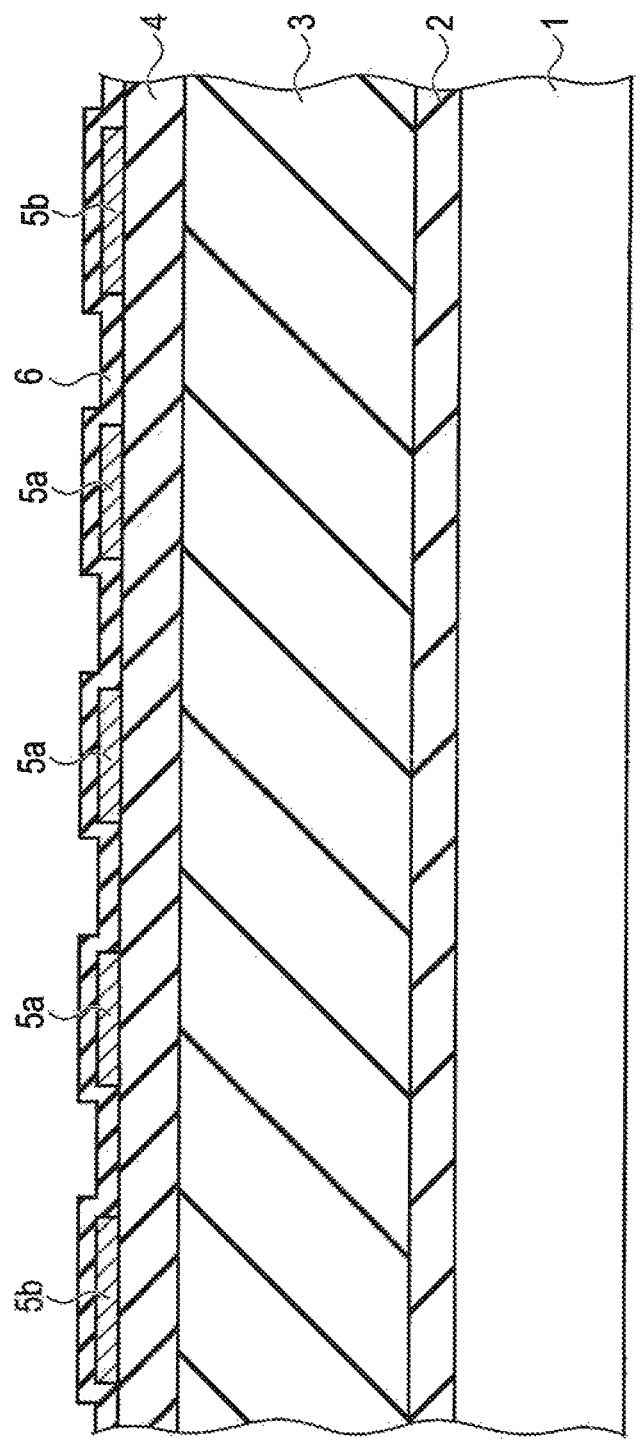
FIG. 4 is a cross-sectional view for explaining the manufacturing method of the hydrogen sensor according to the first embodiment continued from FIG. 3.

Next, as shown in FIG. 4, the insulating layer 6 third insulating layer) is formed on the insulating layer 4 and lower electrode 5a. The insulating layer 4 and the lower electrode 5a are covered with the insulating layer 6. The material for the insulating layer 6 is identical to, for example. The material for the insulating layer 4.

Figure 5:
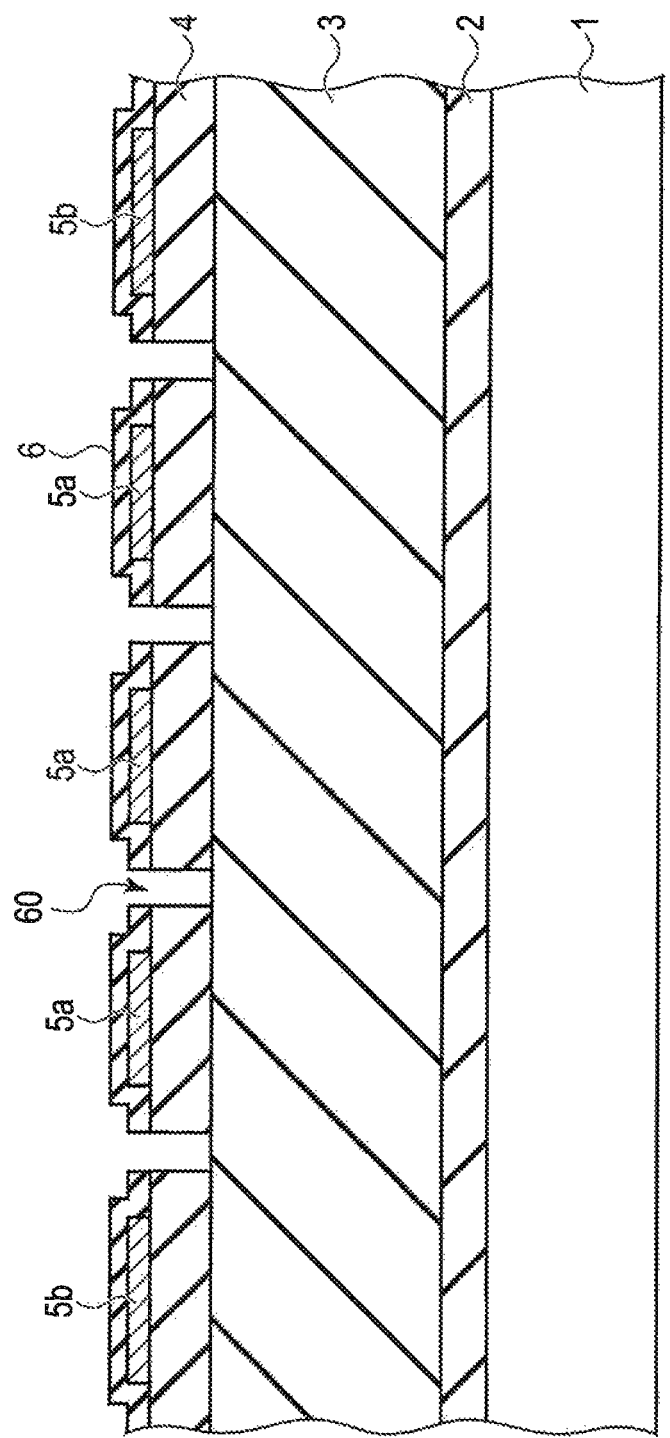
FIG. 5 is a cross-sectional view for explaining the manufacturing method of the hydrogen sensor according to the first embodiment continued from FIG. 4.
Figure 6:
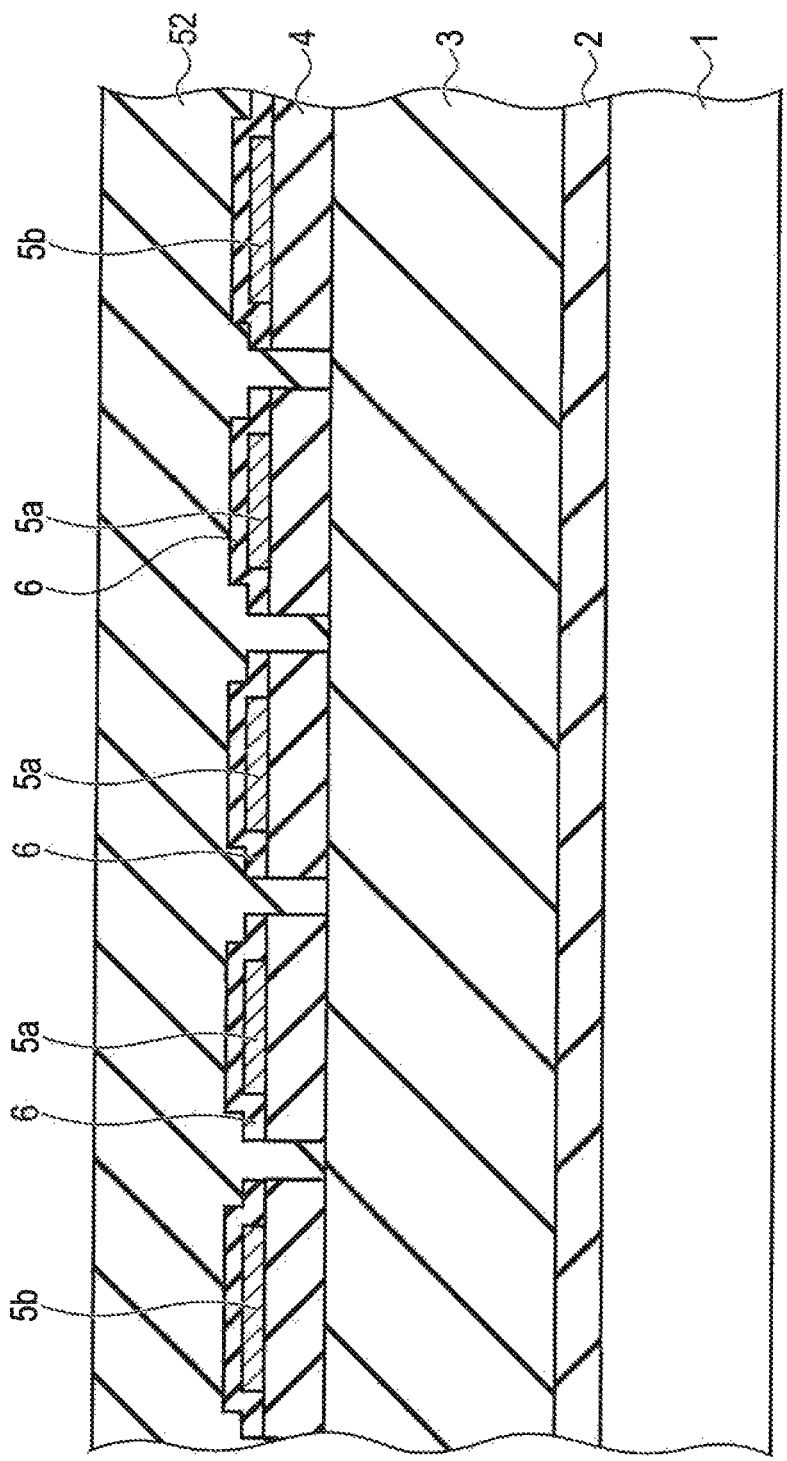
FIG. 6 is a cross-sectional view for explaining the manufacturing method of the hydrogen sensor according to the first embodiment continued from FIG. 5.

Next, as shown in FIG. 5, through holes 60 connected with the insulating layer 3 are formed in the insulating layer 6 and insulating layer 4 by carrying out etching using a resist pattern (not shown) as a mask and, thereafter, as shown in FIG. 6, a sacrificial layer 52 is formed on the insulating layer 6 to thereby infill the through holes 60. A material for the sacrificial layer 52 (fourth insulating layer) is identical to the material for the insulating layer and is, for example, polyimide. At this time, a surface of the sacrificial layer 52 may be planarized by, for example, chemical mechanical polishing (CMP).

Figure 7:
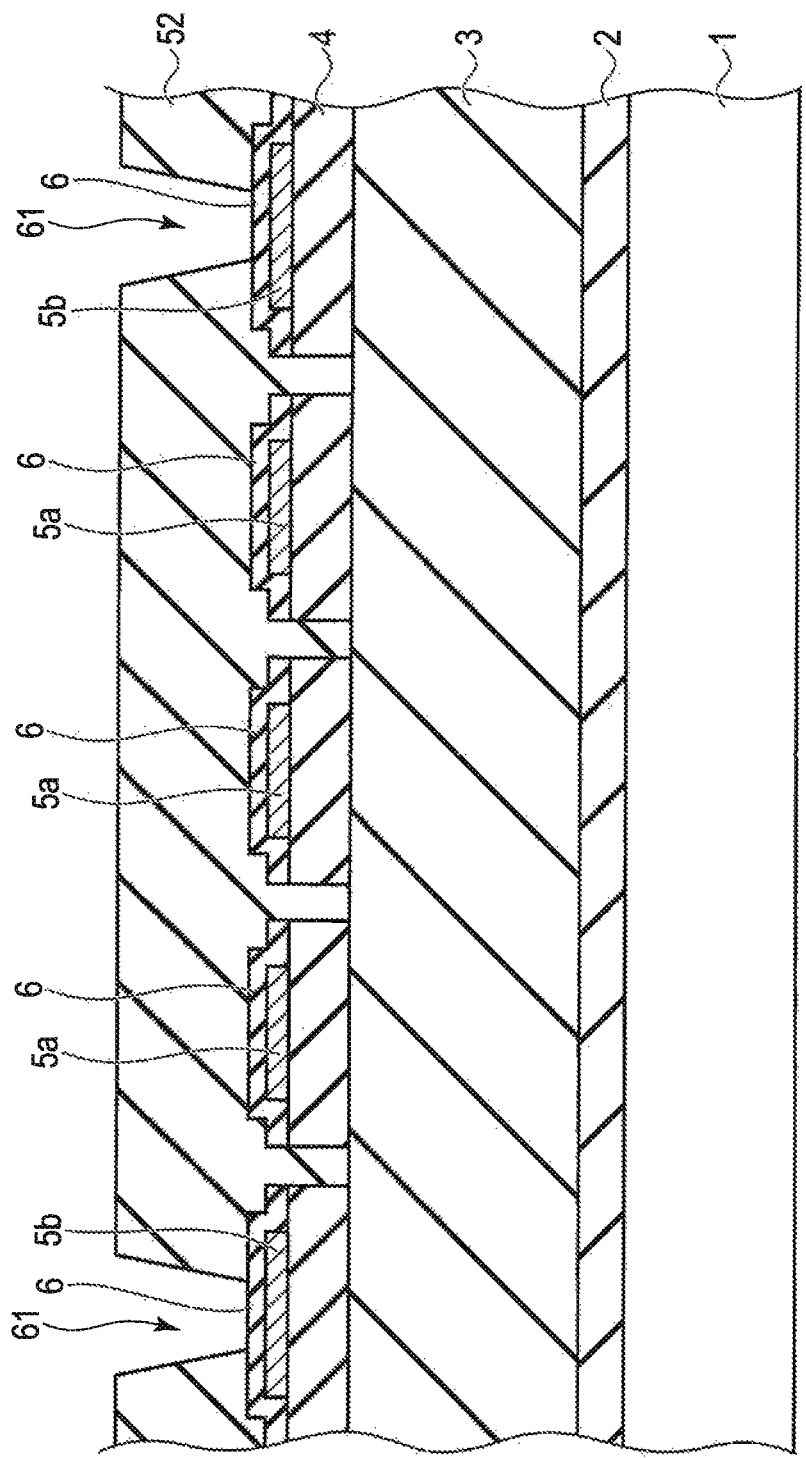
FIG. 7 is a cross-sectional view for explaining the manufacturing method of the hydrogen sensor according to the first embodiment continued from FIG. 6.
Figure 8:
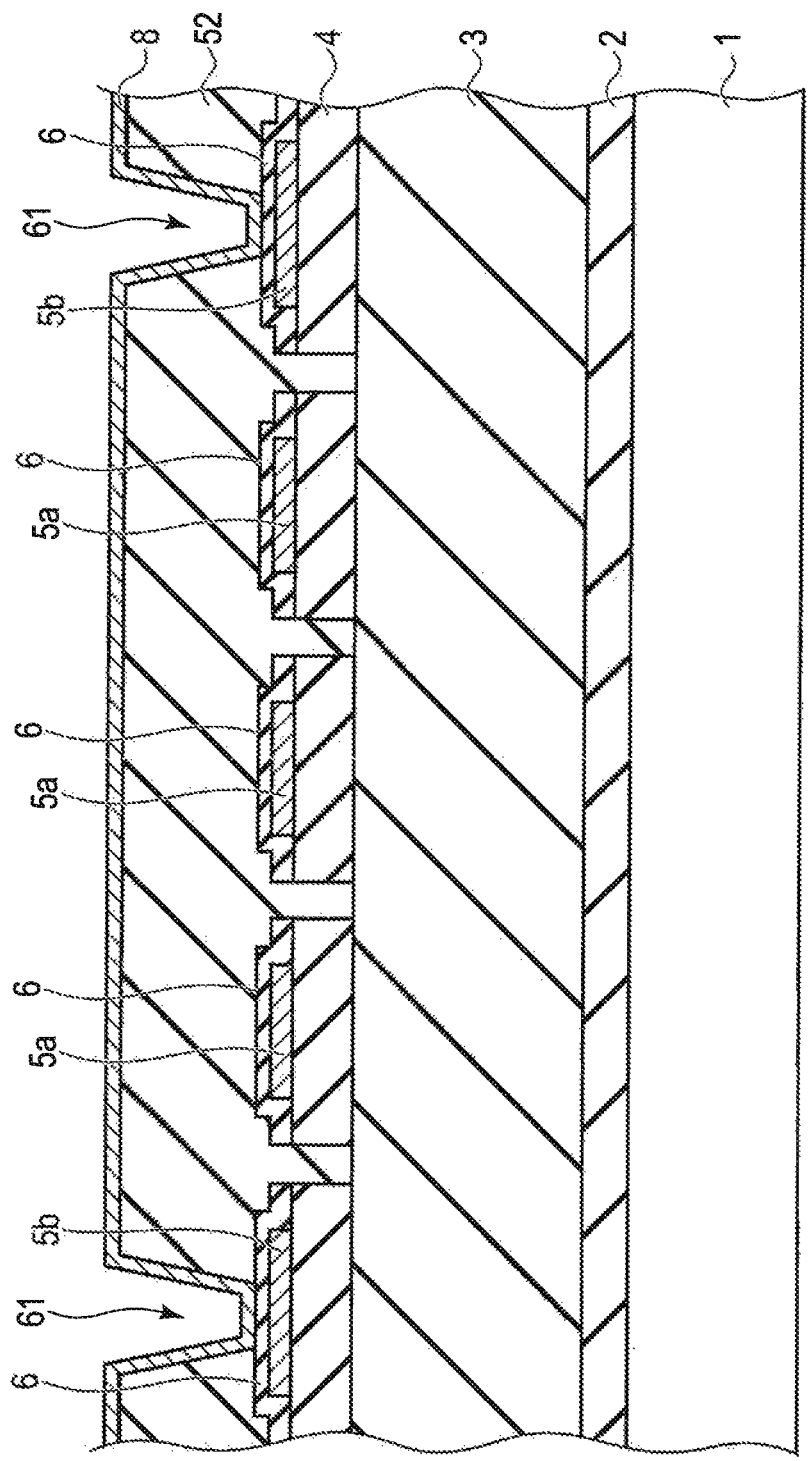
FIG. 8 is a cross-sectional view for explaining the manufacturing method of the hydrogen sensor according to the first embodiment continued from FIG. 7.

Next, as shown in FIG. 7, the sacrificial layer 5 is processed by etching using a resist pattern (not shown) as a mask, whereby through holes 61 connected with the insulating layer 6 on the metallic layer 5b are formed in the sacrificial layer 52, thereafter as shown in FIG. 8, an insulating layer 8 is formed on the entire surface to cover the inner surface (side surface and bottom surface) of each through hole 61. A material for the insulating layer 8 is identical to, for example, the material for the insulating layer 6.

Figure 9:
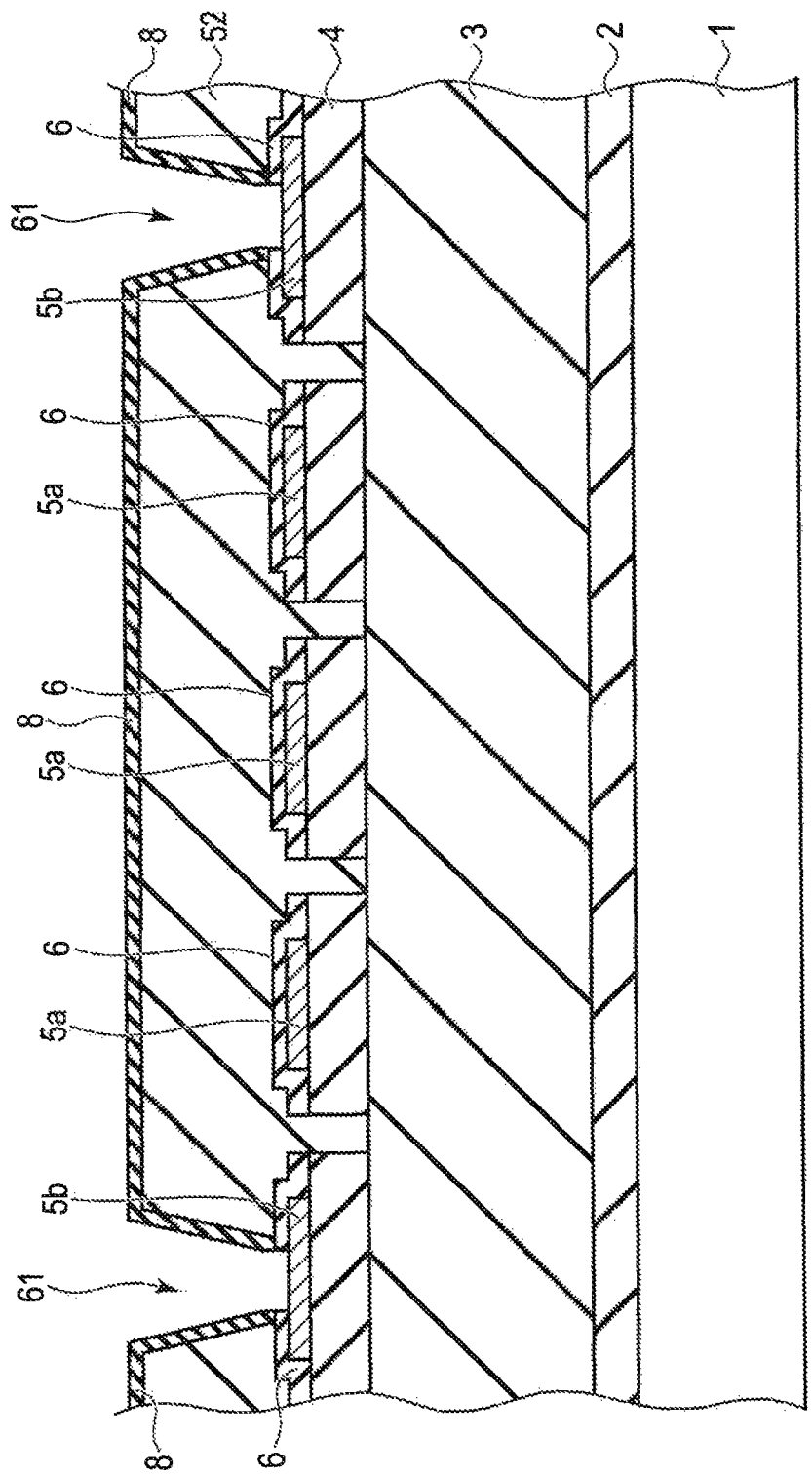
FIG. 9 is a cross-sectional view for explaining the manufacturing method of the hydrogen sensor according to the first embodiment continued from FIG. 8.
Figure 10:
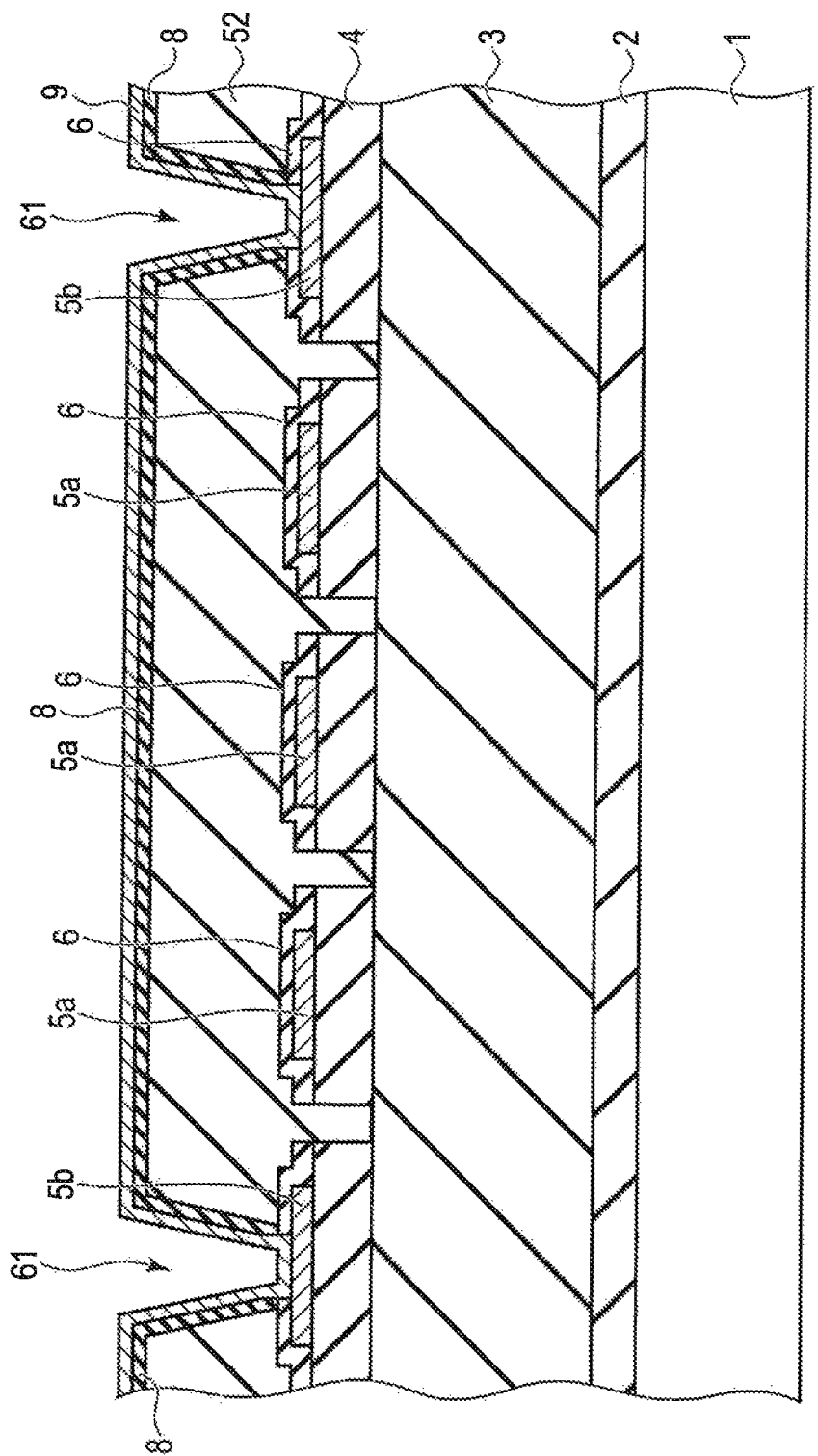
FIG. 10 is a cross-sectional view for explaining the manufacturing method of the hydrogen sensor according to the first embodiment continued from FIG. 9.

Next, as shown in FIG. 9, the insulating layer 6 on the bottoms of the through holes 61 are removed by using photolithography process and etching process, thereby exposing a part of the surface of the metallic layer 5b. Subsequently, as shown in FIG. 10, an electrical conducting layer 9 is formed on the entire surface, which is to be processed into the upper electrode 9a and the anchor 9b shown in FIG. 1. The electrical conducting layer 9 is formed in such a manner that the electrical conducting layer 9 is in contact with the exposed surfaces of the metallic layer 5b on the bottoms of through holes 61, and covers the inner surfaces (side surface and bottom surface) of the through holes 61.

Figure 11:
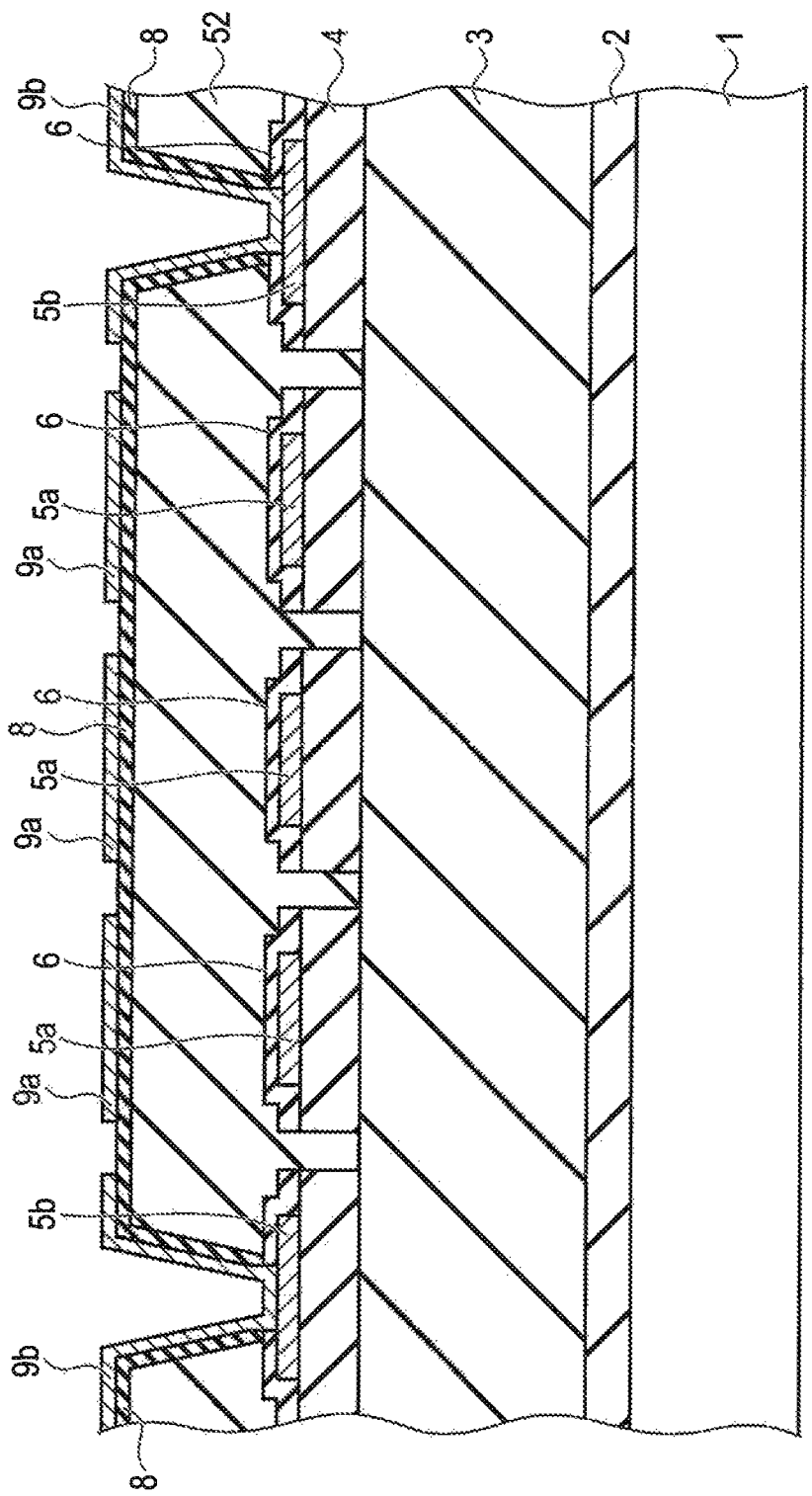
FIG. 11 is a cross-sectional view for explaining the manufacturing method of the hydrogen sensor according to the first embodiment continued from FIG. 10.
Figure 12:
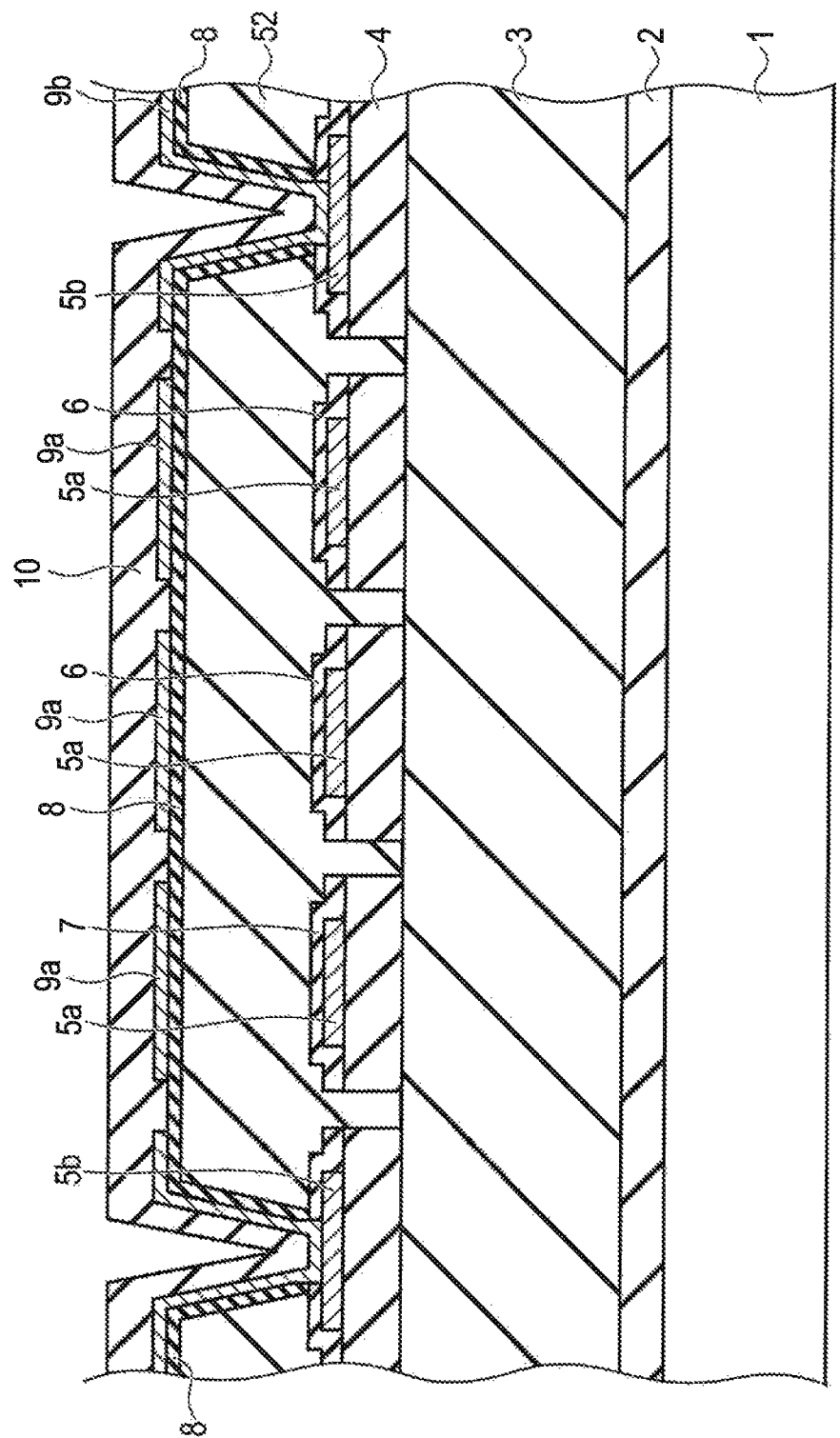
FIG. 12 is a cross-sectional view for explaining the manufacturing method of the hydrogen sensor according to the first embodiment continued from FIG. 11.

Next, the electrical conducting layer 9 and insulating layer 8 are processed by using photolithography process and etching process, whereby the upper electrode 9a and the anchors 9b are formed as shown in FIG. 11.

Figure 13:
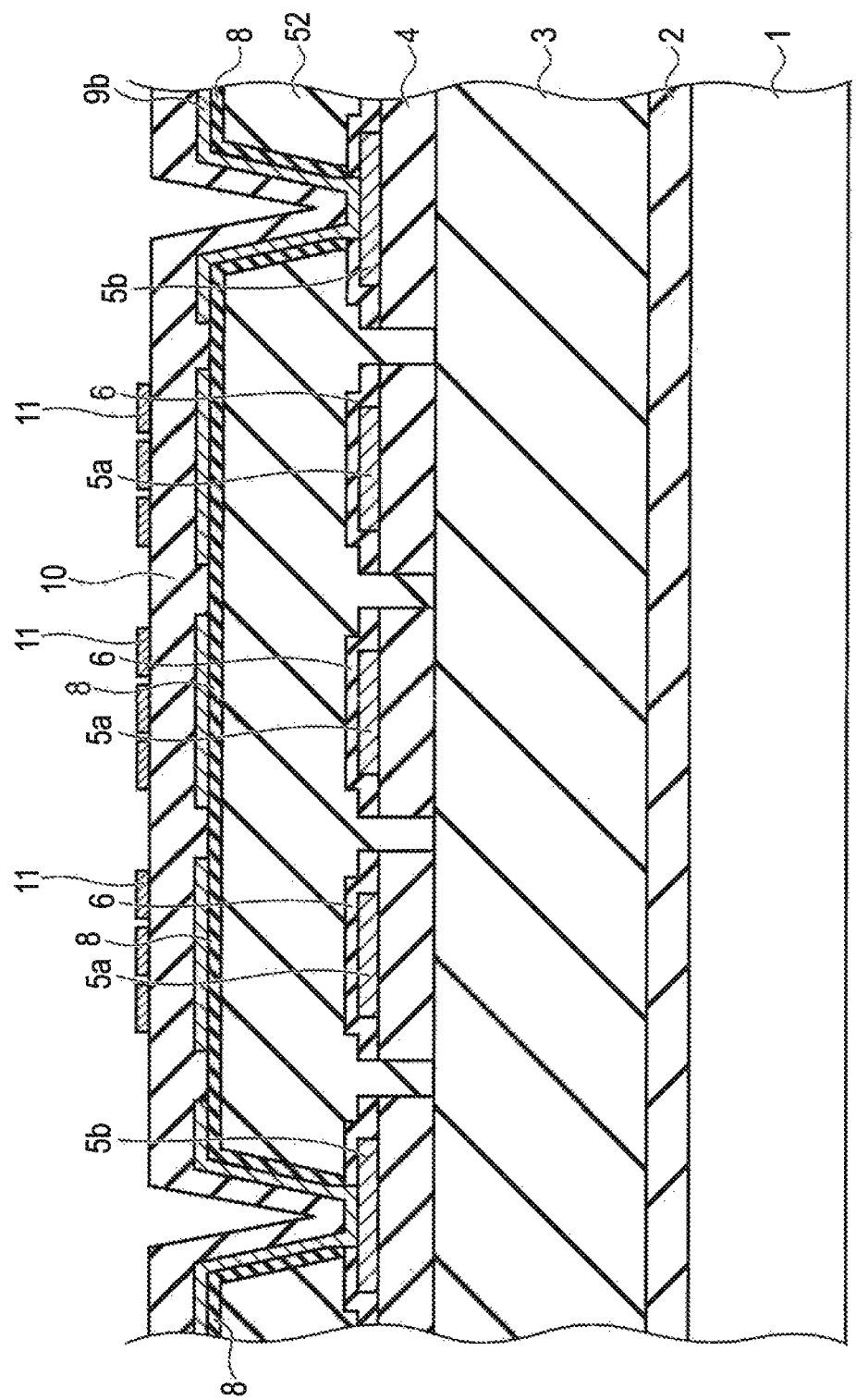
FIG. 13 is a cross-sectional view for explaining the manufacturing method of the hydrogen sensor according to the first embodiment continued from FIG. 12.

As shown in FIG. 13, an insulating layer 10 is formed on the entire surface, which is to be processed into the insulating layers 10a and 10b shown in FIG. 1.

Next, as shown in FIG. 13, the heater 11 is formed on the insulating layer 10. Steps of forming the heater 11 includes, for example, a step of forming an electrical conducting layer (for example, a TiN layer) to be processed into the heater 11, a step of patterning the electrical conducting layer by using photolithography process and etching process. It should be noted that in the cross section of FIG. 13, although the heater 11 seems to be divided into sections, actually, the heater 11 is not divided into sections as shown in FIG. 2C. It should be noted that in FIG. 2C, a reference symbol 200-2 denotes an anchor via (FIG. 22) to be described later, and reference symbol 150 denotes an interconnection (heater bias line) to connect the heater 11 and an interconnection (interconnection 306 in FIG. 22) of the anchor via 200-2 to each other.

Figure 14:
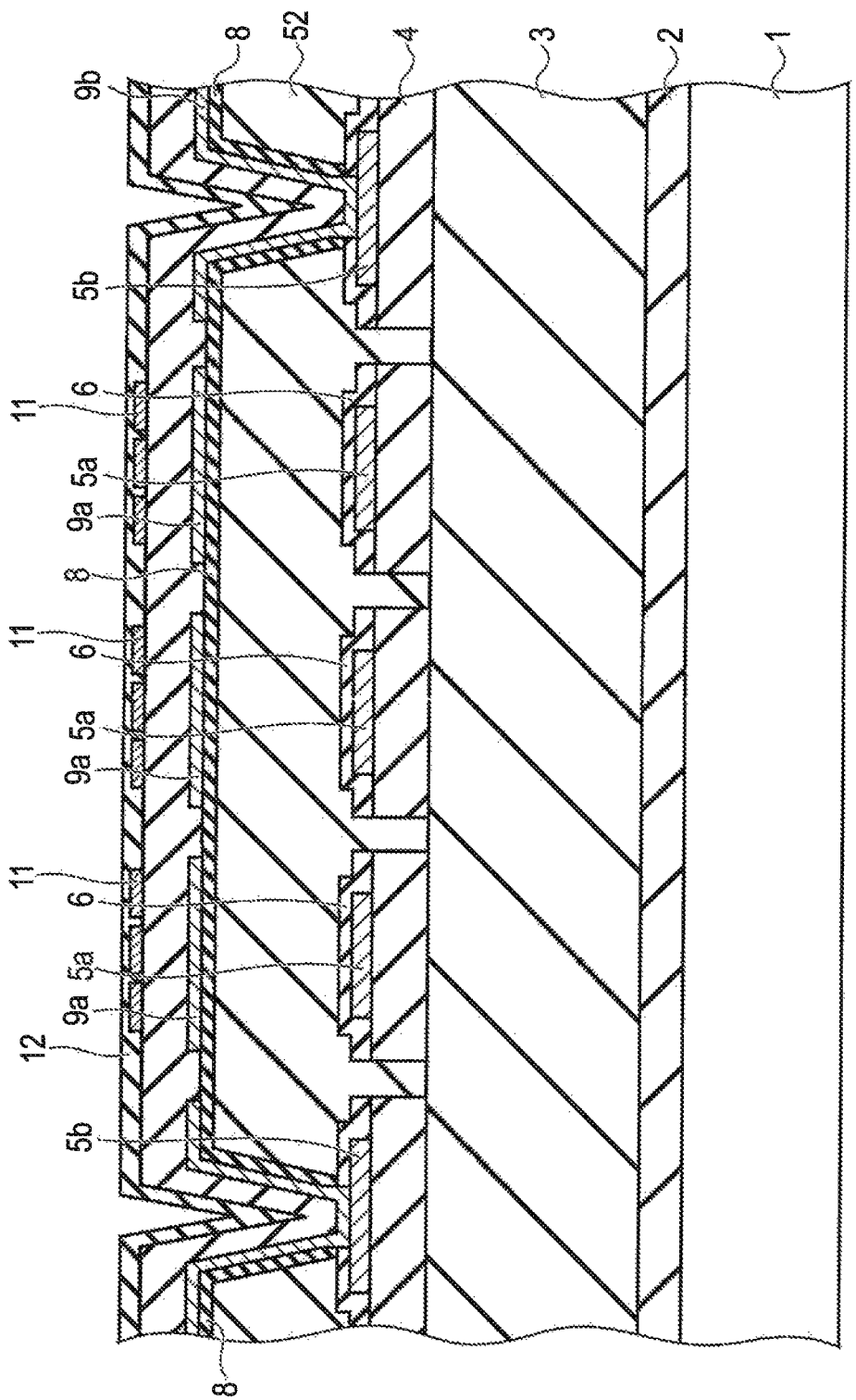
FIG. 14 is a cross-sectional view for explaining the manufacturing method of the hydrogen sensor according to the first embodiment continued from FIG. 13.

Next, as shown in FIG. 14, an insulating layer 12 is formed on the entire surface (insulating layer 10, heater 11) to cover the heater 11. Thereafter, as shown in FIG. 15, a resist pattern (not shown) is formed on the insulating layer 12, and then the insulating layer 12, insulating layer 10 and insulating layer 8a are etched by using the resist pattern as a mask, thereby forming a through hole 62 extending to the surface of the sacrificial layer 52.

Figure 16:
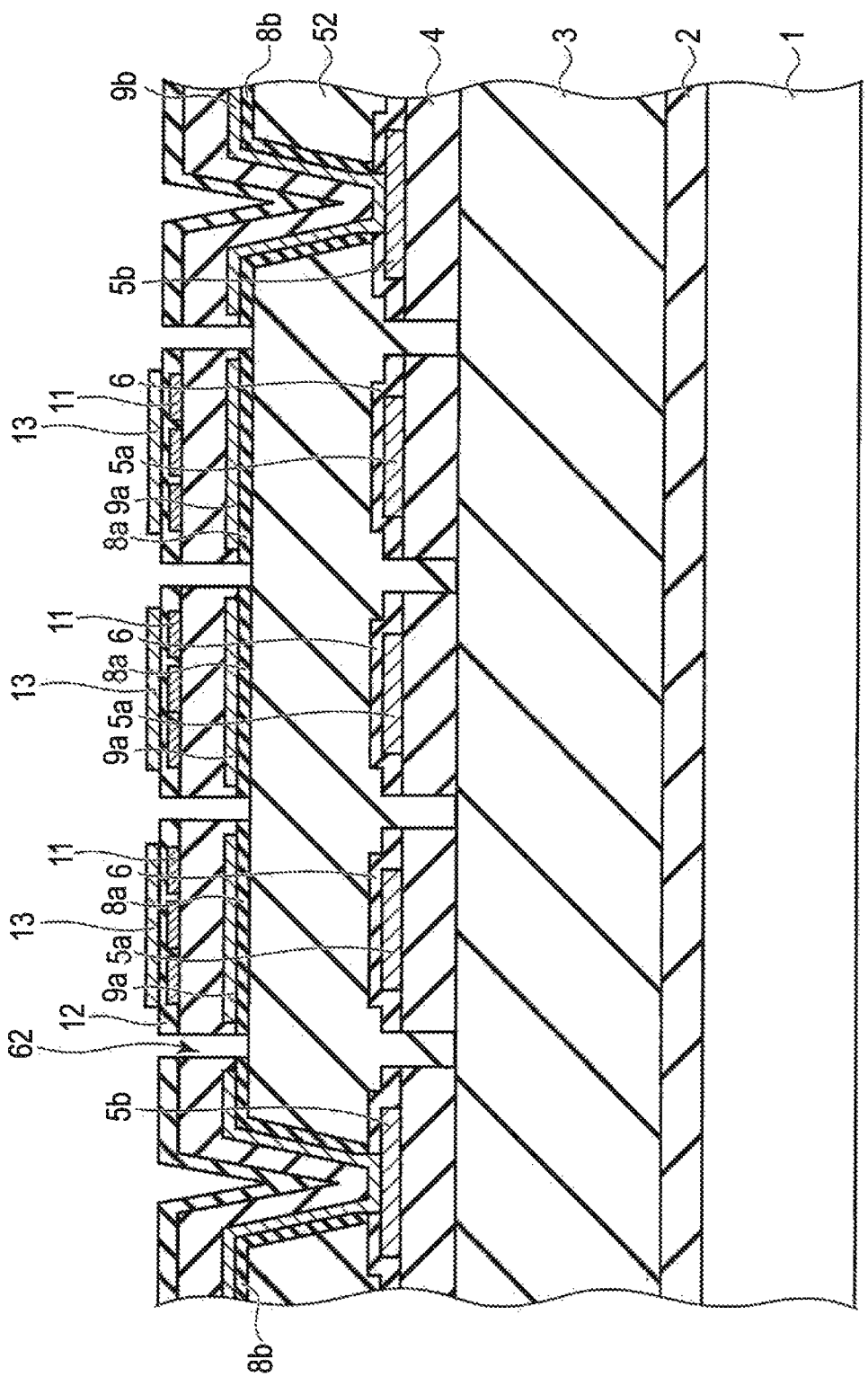
FIG. 16 is a cross-sectional view for explaining the manufacturing method of the hydrogen sensor according to the first embodiment continued from FIG. 15.

Next, as shown in FIG. 16, the hydrogen occlusion layer 13 is formed on the insulating layer 12.

Next, as shown in FIG. 16, the hydrogen occlusion layer 13 is formed on the insulating layer 12, after that, the sacrificial layer 52 and a part of the insulating layer 3 is removed by using, for example, aching (isotropic dry etching) using oxygen ($O_2$), thereby obtaining the hydrogen sensor shown in FIG. 1. The isotropic dry etching may be carried out by using xenon difluoride ($XeF_2$) in place of oxygen ($O_2$).

It should be noted that the entire part of the sacrifice layer 52 can not be removed by using anisotropic etching, and also the part of the insulating layer 3 can not be remove by the using anisotropic etching such that the cavity region 22 shown in FIG. 1 is to be formed. It should be noted that the shape of the cavity region 22 shown in FIG. 1 is an example, and the cavity region 22 may have other shapes. When the isotropic dry etching is employed, the insulating layer 3 is also etched in the lateral direction. This acts to widen the second cavity region 22 in the lateral direction.

Second Embodiment

Figure 17:
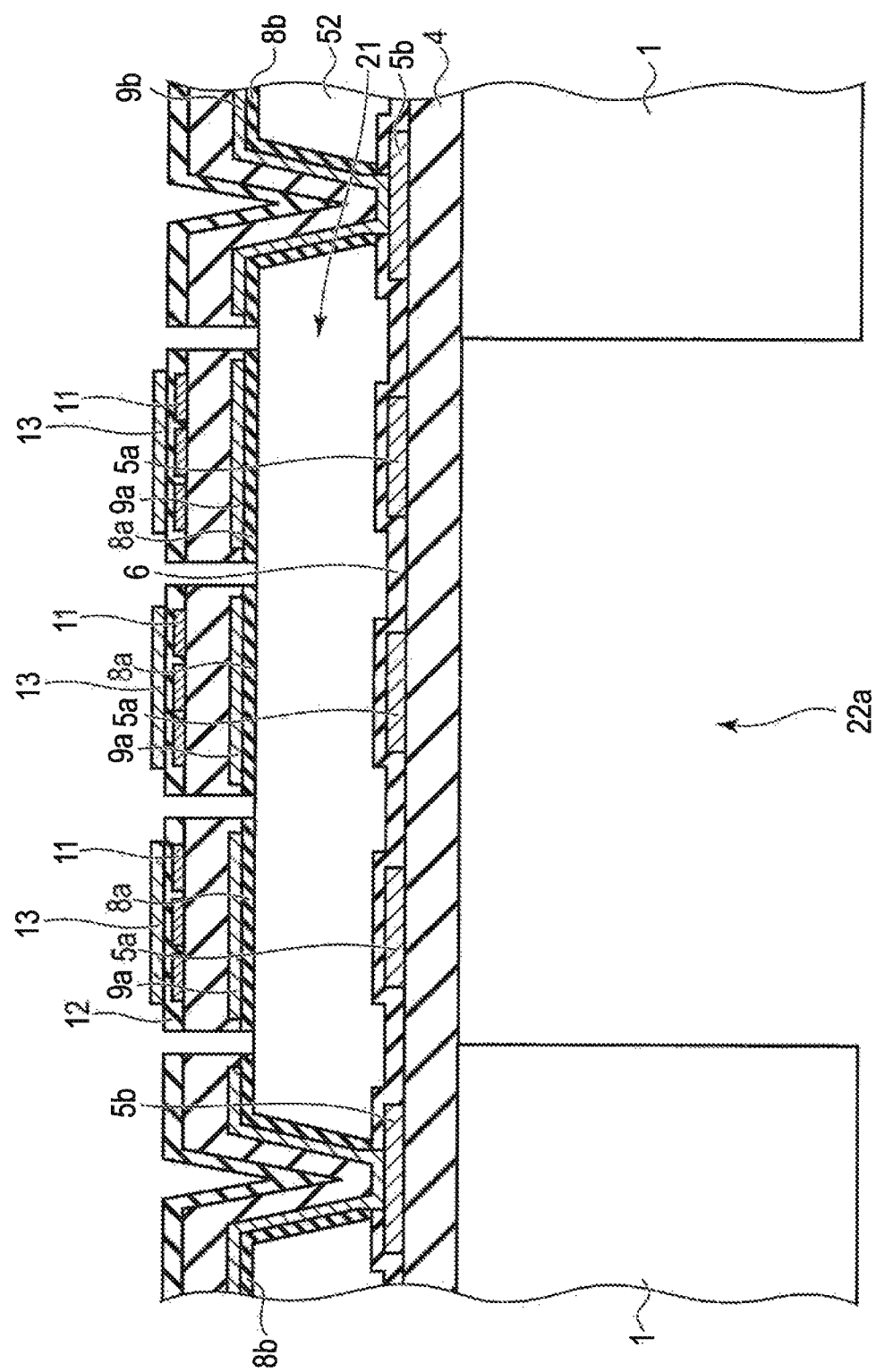
FIG. 17 is a cross-sectional view schematically showing a hydrogen sensor according to a second embodiment.

FIG. 17 is a cross-sectional view schematically showing a hydrogen sensor according to a second embodiment.

The first embodiment employs the cavity region 22 defined by the insulating layer 3 provided with the opening and the insulating layer 4 provided on the insulating layer 3, whereas the present embodiment employs a cavity region 22a defined by a through hole provided in the silicon substrate 1. There exists air in the cavity region 22a. The air has high thermal resistance. When the insulating layers 4 and 6 are formed thin, the cavity region 22a is substantially connected in series to the cavity region 21, and thus the cavity region 22a functions in the same manner as the cavity region 22. It should be noted that the cavity region 22a may be connected in series to the cavity region 21 through the through holes as in the case of the first embodiment.

In the first embodiment, the insulating layers 2 and 3 are provided on the silicon substrate 1, whereas in the present embodiment, the insulating layers 2 and 3 are not provided in order to facilitate formation of the cavity region 22a.

Figure 18:
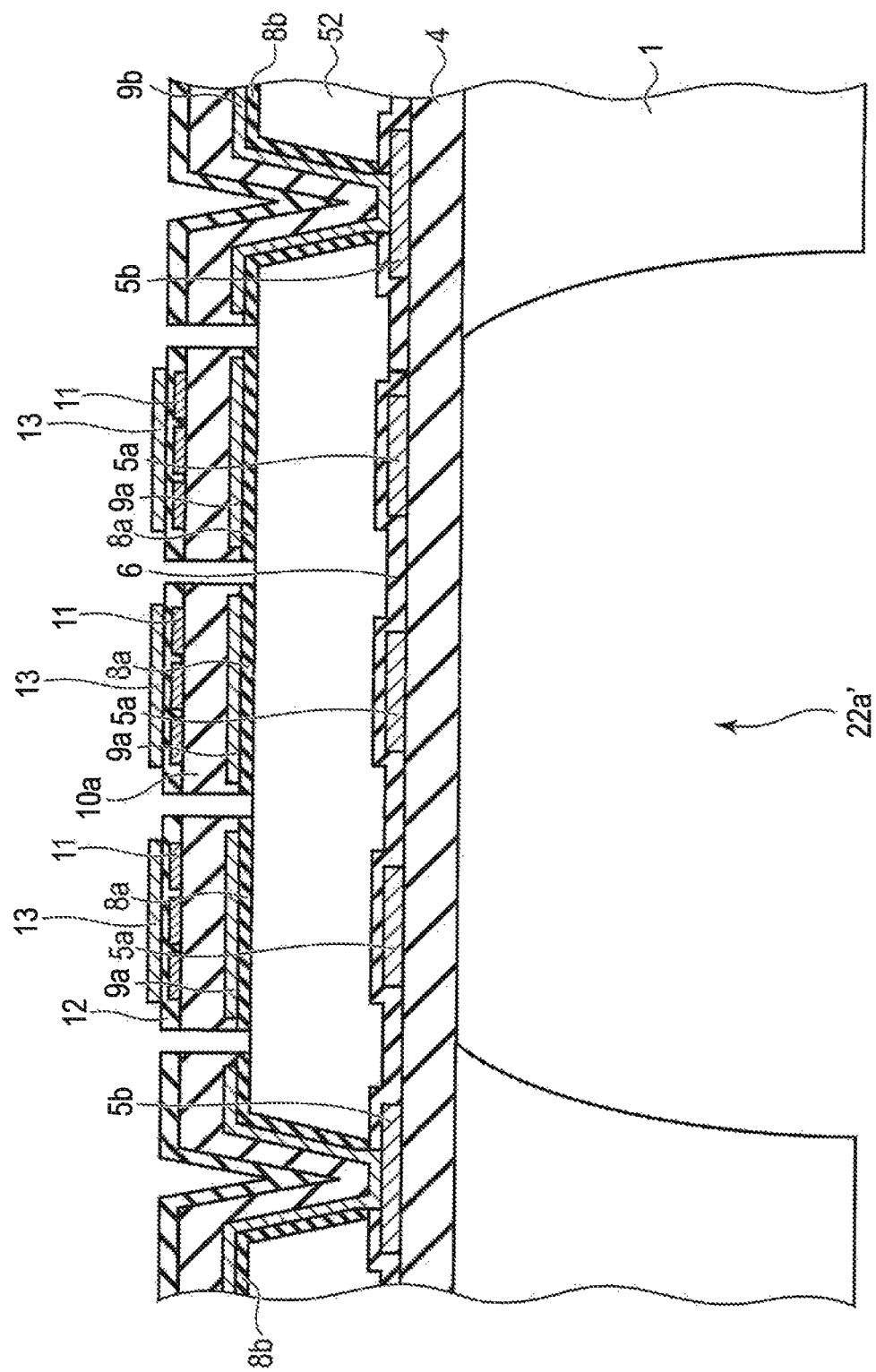
FIG. 18 is a cross-sectional view schematically showing a modification example of the hydrogen sensor according to the second embodiment.

The cavity region 22a can be performed by, for example, etching the silicon substrate 1 from the rear surface thereof in the step of FIG. 6 (except for that the insulating layers 2 and 3 are not formed). In FIG. 17, the cavity region 22a having a shape formed by the anisotropic etching is shown, however a cavity region 22a' formed by the isotropic etching as shown in FIG. 18 may be used. FIG. 18 shows the cavity region 22a' in which the shape of the side surface is determined by a curved line, however the shape of the side surface may be determined by a straight line, or a combination of a straight line and a curved line.

Third Embodiment

Figure 19:
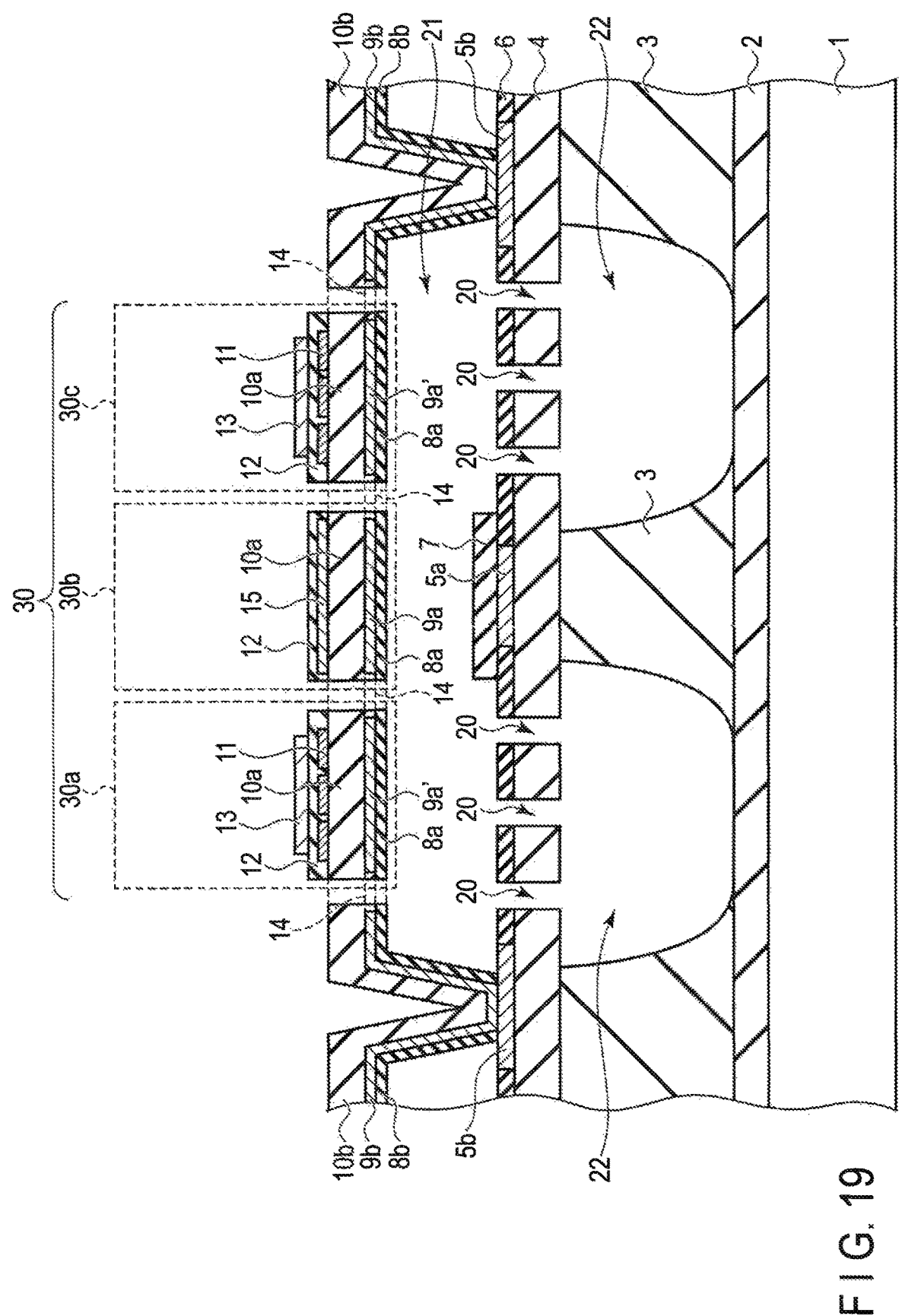
FIG. 19 is a cross-sectional view schematically showing a hydrogen sensor according to a third embodiment.

FIG. 19 is a cross-sectional view schematically showing a hydrogen sensor according to a third embodiment.

A movable structure 30 of the hydrogen sensor according to the present embodiment includes two hydrogen actuators 30a and 30c, and one upper electrode section 30b provided between the hydrogen actuators 30a and 30c. One end part of the upper electrode section 30b is connected to the hydrogen actuator 30a through a spring section 14. Likewise, the other end part of the upper electrode section 30b is connected to the hydrogen actuator 30c through a spring section 14.

The upper electrode section 30b has a structure corresponding to the movable structure 30 in FIG. 1 except for that the hydrogen absorption 13 is omitted and an electrical conducting layer (dummy metal) is provided instead of the heater 11. A material for the electrical conducting layer 15 is same as the material for the heater 11, however the electrical conducting layer 15 is not connected to a power source, and thus does not function as the heater.

The electrical conducting layer 15 is provided for the purpose of suppressing warpage of the insulating layer 10a caused by residual stress of the insulating layer 10a. To achieve the above purpose, the electrical conducting layer 15 preferably has the same shape and dimensions as the upper electrode 9a. In the hydrogen sensor according to the present embodiment the distance between the lower electrode 5a and upper electrode 9a is not changed only by the upper electrode section 30b. The upper electrode section 30h does not include the heater 11 and hydrogen occlusion layer 13, because the upper electrode section 30b does not require the structure to increase the thermal resistance. The upper electrode section 30b is connected to an external circuit (not shown).

The hydrogen actuators 30a and 30c each has the similar structure as the movable structure 30 except for that a dummy electrode 9a' is provided instead of the upper electrode 9a. The lower electrode is not provided below the dummy electrode 9a', so that the dummy electrode 9a' does not functions as the upper electrode 9 constituting the capacitor. The dummy electrodes 9a' have a function of suppressing warpages of the insulating layers 10a in the hydrogen actuators 30a and 30c, which are caused by the residual stress of the insulating layers 10a. The shape of the dummy electrode 9a' is, for example, a plate-like shape or mesh-like shape.

The second cavity region 22 is provided below each of the hydrogen actuators 30a. and 30c. Upon absorption of hydrogen, each of the hydrogen actuators 30a and 30c is deformed as in the case of the movable structure 30. Therefore, in the hydrogen sensor according to the present embodiment, the deformations of the hydrogen actuators 30a and 30c cause a change of the distance between the lower electrode 5a and the upper electrode 9a in the upper electrode portion 30a.

The similar effect as the first embodiment is also obtained in the present embodiment. In addition, the power consumption can be further reduced because the number of heater 11 in the movable structure can be reduced.

Figure 20:
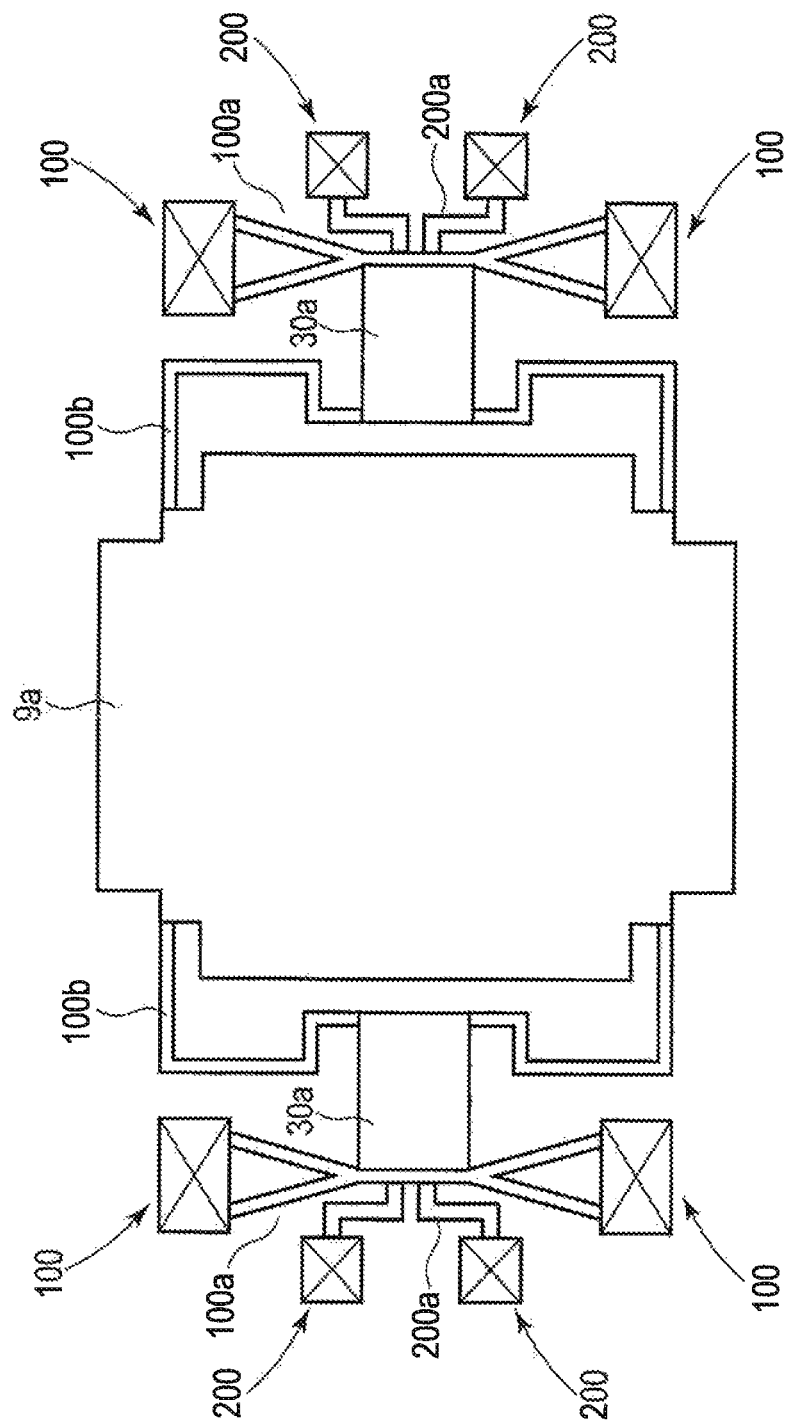
FIG. 20 is a plan view schematically showing the hydrogen sensor according to the third embodiment.

FIG. 20 shows an example of a plan view schematically showing the hydrogen sensor of the present embodiment. In FIG. 20, a reference symbol 100 denotes an anchor, and corresponds to 9b in FIG. 10. Further, a reference symbol 100a denotes a spring section connecting the anchor 100 and hydrogen actuator 30a to each other, and corresponds to the spring section 14 in FIG. 1.

Figure 26:
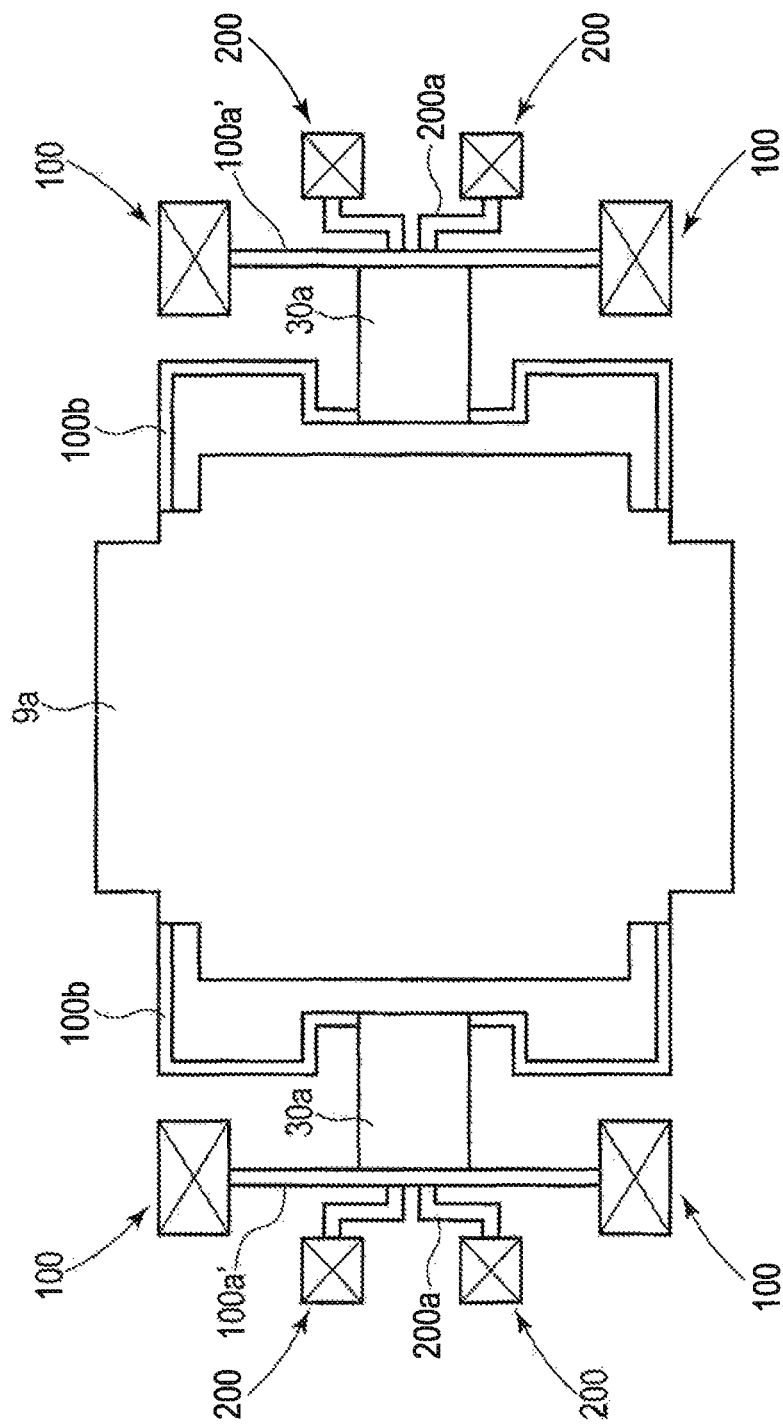
FIG. 26 is a plan view schematically showing a modification example of the hydrogen sensor according to the third embodiment.

The thermal resistance of the spring section 100a is, for example, about ten times as large as the total thermal resistance of the cavity regions 21 and 22. Accordingly, the thermal resistance of the spring section 100a is sufficiently large. In general, a member having large thermal resistance has a small mechanical spring constant and is soft. If the spring constant of the spring section 100a connected to each of the hydrogen actuators 30a and 30c is small, the deformation of the hydrogen actuator becomes difficult to be transmit to the movable electrode section 30b of the capacitance section, and thus, for example, when the detection of hydrogen is performed, the sensitivity for detecting hydrogen becomes worse. Accordingly, in order to effectively transmit the deformation of each of the hydrogen actuators 30a and 30c to the upper electrode section 30b, it is necessary to determine the shape and physical properties of the spring section 100a in such a manner that the ends of the spring section 100a becomes pseudo mechanical fixed ends. From that point of view, it is necessary for the shape of the spring 100a to include a straight shape that is a shape without a turn, and in FIG. 20, the spring 100a has a shape in which two Y-shaped sprig sections are connected to each other. Further, in order to enhance the effect of the straight shape, the spring section 100a has a tensile stress with respect to the semiconductor substrate 1. Further, in order to enhance the effect of the straight shape, the spring section 100a has a tensile stress with respect to the semiconductor substrate 1. The Y-shaped shape is employed to prevent the spring portion 100a from being rotated even the hydrogen actuator 30a absorbs hydrogen and deforms. When the spring section 100a can be prevented from being rotated, a straight shape spring portion 100a' shown in FIG. 26 may be used A reference symbol 100b denotes a spring section configured to connect the hydrogen actuator 30a and upper electrode 9a (through holes not shown) to each other. The thermal resistance of the spring section 100b formed by using a general process is, for example, about ten times as large as the total thermal resistance of the cavity regions 21 and 22, but the spring section 100b is not required to have the function of the pseudo fixed end, and thus the spring section 100b does not need to have the straight shape unlike the spring section 100a. A reference symbol 200 denotes an anchor configured to connect the heater in the hydrogen actuator 30a to an external circuit (not shown). A reference symbol 200a denotes a spring section configured to connect the anchor 200 and hydrogen actuator 30a to each other.

FIG. 21A is a cross-sectional view showing the upper electrode 9a and an example of a structure under the upper electrode 9a. The exemplary structure includes a TiN layer 9a1 and a SiN layer 9a2 which are stacked in sequence. The thicknesses of the TiN layer 9a1, the SiN layer 9a2, and the upper electrode 9a are, for example, 50 nm, 3 μm, and 50 nm, respectively. The width of each of the TiN layer 9a1, the SiN layer 9a2, and the upper electrode 9a is, for example, 6 μm.

Note that, in order to prevent oxidization of the TiN layers 9a and 9a1, insulating films (protective films) are actually provided on an upper surface, a lower surface and a side surface of the TiN layers 9a, and those of the TiN layer 9a1, but in FIG. 21A, the insulating films are omitted for the purpose of simplicity. The insulating film described above is a thin insulating film having a thickness of about 100 nm, and a material for the insulating film is, for example, silicon nitride. Likewise, the insulating films on the upper surfaces, lower surfaces, and side surfaces of the TiN layers in FIG. 21B, FIG. 21D, and FIG. 21E are also omitted. Further, TiN of each of FIG. 21A, FIG. 21B, FIG. 21D, and FIG. 21E is an example of an electrical conducting material, and other electrical conducting materials may also be used. For example, Ti may be used as in the case of the TiN layer (upper electrode) 9a.

FIG. 21B is a cross-sectional view showing an example of the structure of the hydrogen actuator 30a. The structure includes a stacked structure in which a TiN layer 30a1, a SiN layer 30a2, a TiN layer (heater) 30a3, and a Pd layer (hydrogen occlusion layer) 30a4 are stacked in sequence. The thicknesses of the TiN layer 30a1, SiN layer 30a2, TiN layer 30a3, and Pd layer 30a4 are, for example, 50 nm, 3 μm, 45 nm, and 500 nm, respectively.

FIG. 21C is a cross-sectional view showing an example of the structure of the spring section 100a. The structure includes the SiN layer 100a1. The thickness and width of the SiN layer 100a1 are, for example, 3 μm, and 6 μm, respectively.

FIG. 21(d) is a cross-sectional view showing an example of the structure of the spring section 100b. The structure includes a stacked structure in which a TiN layer 100b1, and SiN layer 100b2 are stacked in sequence. The thicknesses of the TiN layer 100b1, and SiN layer 100b2 are, for example, 50 nm, and 3 μm, respectively. The width of each of the TiN layer 100b1, and SiN layer 100b2 is, for example, 6 μm.

FIG. 21(e) is a cross-sectional view showing an example of the structure of the spring section 200a. The structure concerned includes a stacked structure in which a TiN layer 200a1, SiN layer 200a2, and TiN layer 200a3 are stacked in sequence. The thicknesses of the TiN layer 200a1, SiN layer 200a2, and TiN layer 200a3 are, for example, 50 nm, 3 μm, and 50 nm, respectively. The width of each of the TiN layer 200a1, SiN layer 200a2, and TiN layer 200a3 is, for example, 8 μm or 6 μm.

Figure 22:
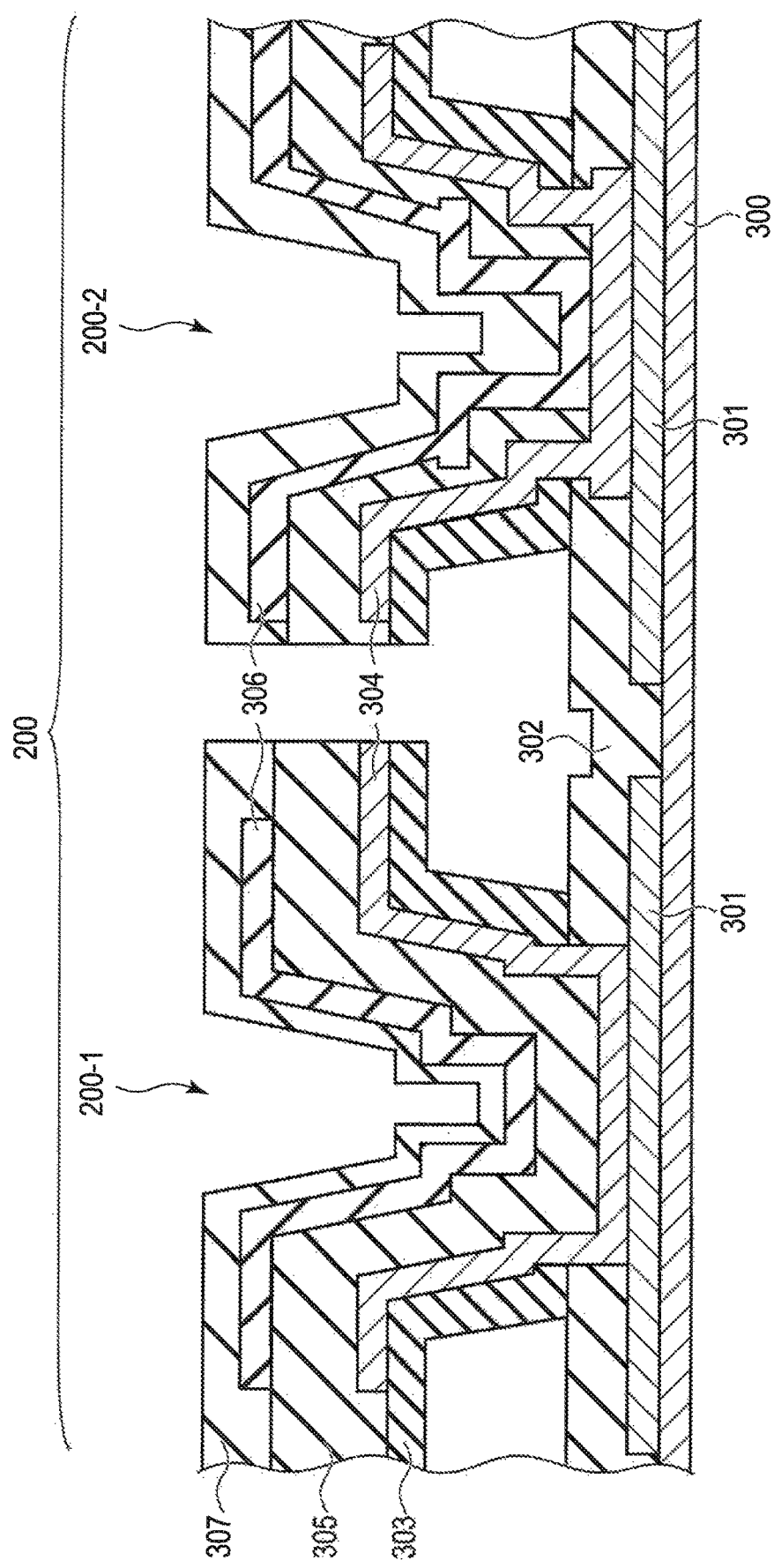
FIG. 22 is a cross-sectional view for explaining an anchor via of the hydrogen sensor according to the third embodiment.

FIG. 22 is a cross-sectional view showing the more detailed structure of the anchor 200. The anchor 200 includes an anchor via 200-1 for an extraction interconnection of the upper electrode, and anchor via 200-2 for an extraction interconnection of the heater.

In FIG. 22, reference symbols 300, 302, 303, 305, and 307 denote insulating layers. A reference symbol 301 denotes an interconnection formed in the step that is same as that of the lower electrode, and reference symbol 304 denotes an interconnection formed in the same step that is same as that of the upper electrode, and reference symbol 306 denotes an interconnection formed in the same step that is same as that of the heater.

In the anchor via 200-1 for the extraction interconnection of the upper electrode, the interconnection 304 and the interconnection 306 are electrically isolated from each other by an insulating layer 305. Further, in the anchor via 200-1, the rightmost end part of the interconnection 304 is connected to the upper electrode (not shown). The interconnection 304 is connected to an external circuit (power source) through the interconnection 301.

In the anchor via 200-2 for the extraction interconnection of the heater, the interconnection 304 and interconnection 306 are electrically connected to each other. Further, in the anchor via 200-2, the rightmost end part of the interconnection 306 is connected to the heater (not shown). The interconnection 306 is connected to an external circuit (power source) through the interconnection 304 and interconnection 301.

It should be noted that in the present embodiment, although the number of the hydrogen actuators is two, the number of the hydrogen actuators may be one or three or more.

Fourth Embodiment

Figure 23:
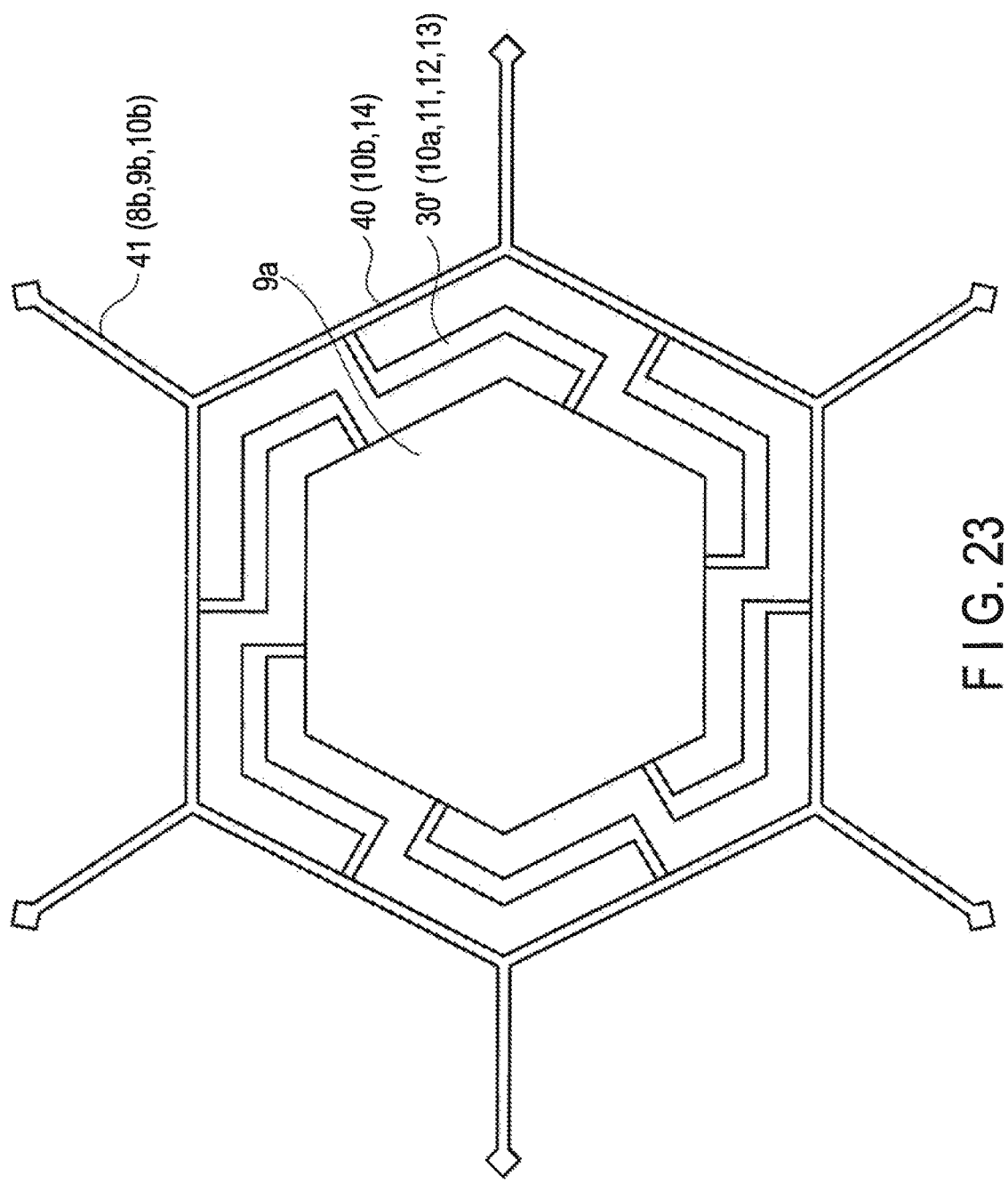
FIG. 23 is a plan view schematically showing a hydrogen sensor according to a fourth embodiment.

FIG. 23 is a plan view schematically showing a hydrogen sensor according to a fourth embodiment. The cross-sectional view of the hydrogen sensor of the present embodiment corresponds to, for example, the cross-sectional view of FIG. 19 (third embodiment). That is, the hydrogen sensor of the present embodiment relates to a hydrogen sensor in which the movable structure is divided into a hydrogen actuator and an upper electrode section, and the plane pattern (planar shape) of the hydrogen sensor of the present embodiment is different from that of the third embodiment.

An upper electrode 9a has a hexagonal (polygonal) shape. The upper surface and lower surface of the upper electrode 9a are flat.

An annular beam structure 40 constituted of six straight members is provided around a second electrode. That is, the beam structure 40 includes straight members of the number identical to the number of the sides defining the polygon of the upper electrode 9a. Each of the straight members includes the insulating layer 10b and the spring section 14 which are described in the first embodiment and the like.

Six movable structures 30' are provided between the upper electrode 9a and the beam structure 40. The movable structure 30' is that obtained by omitting the upper electrode 9a from the movable structure 30 described in the first embodiment and the like, and thus includes the members such as an insulating layer 10a, a heater 11, an insulating layer 12, a hydrogen occlusion layer 13, and the like. It should be noted that in FIG. 23, a reference symbol 30' is attached to only one movable structure for the sake of simplification. Each one end part of the different movable structures 30' is connected to a respective different part of the upper electrode 9a. Each other end part, of the different movable structures 30' is connected to a respective different part of the upper electrode 9a. The number of the movable structure 30' is identical to the number of the sides defining the polygon of the upper electrode 9a.

Further, parts corresponding to the six vertexes of the beam structure 40 are respectively connected to different supporting structures 41. Each of the supporting structures 41 includes the insulating layer 8b, the anchor 9 and the insulating layer 10b which are explained in the first embodiment, and the like.

In the present embodiment, the upper electrode 9a, the beam structure 40, the six movable structures 30', and the supporting structures 41 constitute a symmetrical structure when these members are viewed from above the upper electrode 9a. The structure of FIG. 23 has a rotational symmetry.

Both the insulating layer 10a of the movable structure 30' and the insulating layer 10b of the beam structure 40 are, for example, silicon nitride layers. In the present embodiment, the silicon nitride layer used as the insulating layer 10b of the beam structure 40 has a tensile stress with respect to the substrate 1. As a result, the part of the movable structure 30' connected to the beam structure 40 functions as a pseudo fixed end, and thus hence it becomes possible to obtain a high detection sensitivity. The spring portion 14 preferably includes a material that increases the tensile stress of the beam structure 40. In the present embodiment, the movable structure 30' is connected to the beam structure 40 having high thermal resistance, thereby enabling reduction of the electric power required for the heater (not shown) to heat the hydrogen occlusion layer (not shown) in the movable structure 30'. Therefore, according to the present embodiment, it becomes possible to provide a hydrogen sensor having sufficient performance (high detection sensitivity and low power consumption).

Furthermore, in the present embodiment, the structure constituted of the upper electrode 9a, six movable structures 30', beam structure 40, and supporting structures 41 has the rotational symmetry. For that reason, when the distance between the upper electrode 9a and the lower electrode (not shown) is changed by the expansion of the hydrogen occlusion layer (deformation of the movable structure 30') that is caused by heating the hydrogen occlusion layer by the heater, the upper electrode 9a only rotates by a predetermined angle with respect to an axis (rotational axis) that is perpendicular to the flat upper surface of the upper electrode 9a. That is, the distance between the upper electrode 9a and the lower electrode is suppressed from being changed with position due to inclination of the lower surface of the upper electrode 9a relative to the flat upper surface of the lower electrode. Thereby enabling suppression of the reduction of the detection sensitivity.

It is noted that the gas sensor according to the present embodiment includes the silicon substrate 1, the fixed electrode 5a and the first cavity region 21 and the like as in the cases of the first to fourth embodiments, but the sensor may include or may not include the second cavity region 22.

In addition, in the present embodiment, the shapes of the upper electrode 9a and the movable structure 30' are hexagon, but other polygons may be used. Regular polygon is preferably employed in order to achieve the symmetrical structure. It is desirable to employ a regular polygon for the symmetrical structure.

Figure 24:
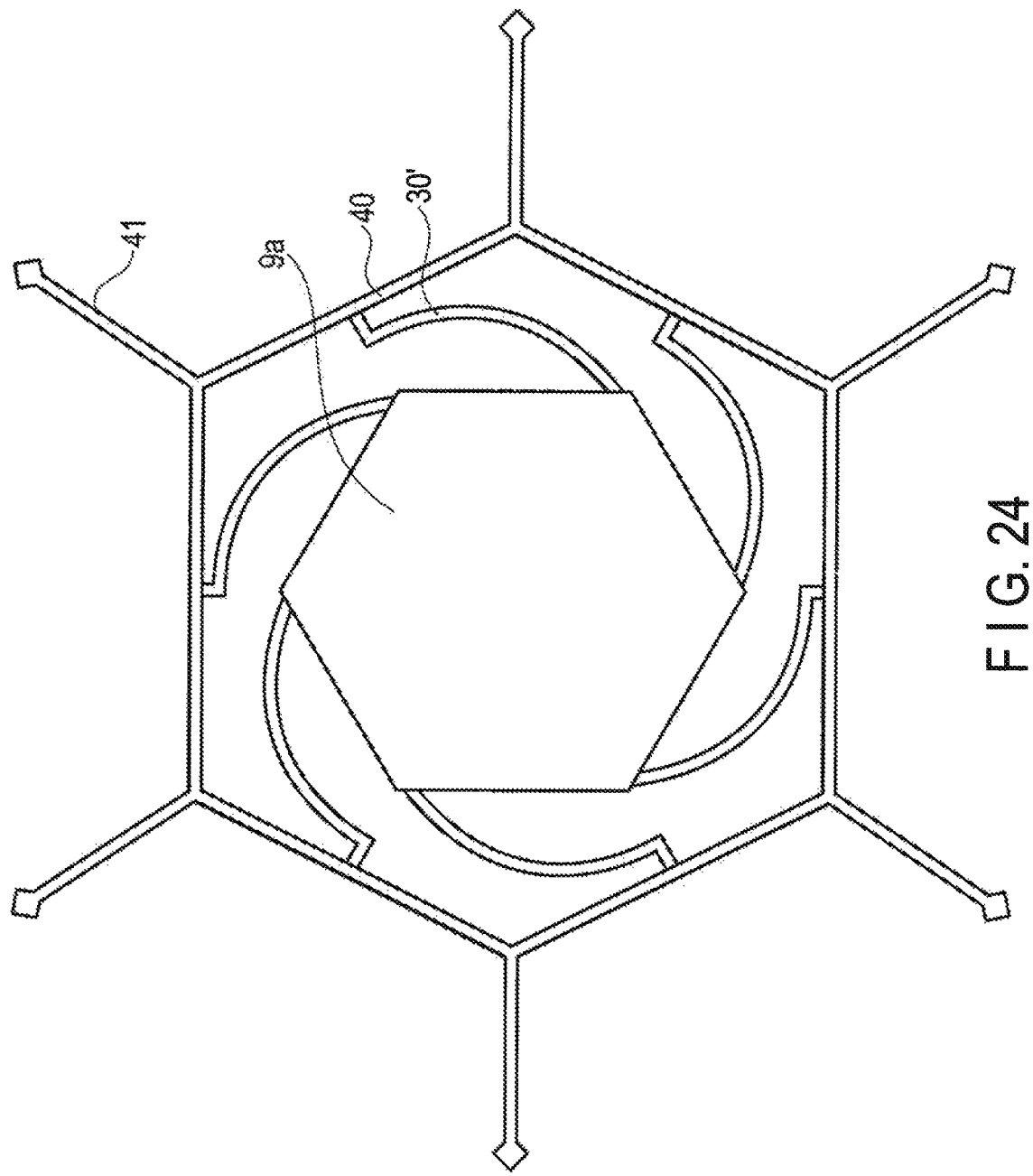
FIG. 24 is a plan view schematically showing a modification example of the hydrogen sensor according to the fourth embodiment.

Further, in the present embodiment, although the movable structure 30' has the shape constituted of the straight members, the movable structure 30' may also have a shape constituted of a member including a curvilinear shape as shown in FIG. 24.

Fifth Embodiment

Figure 25:
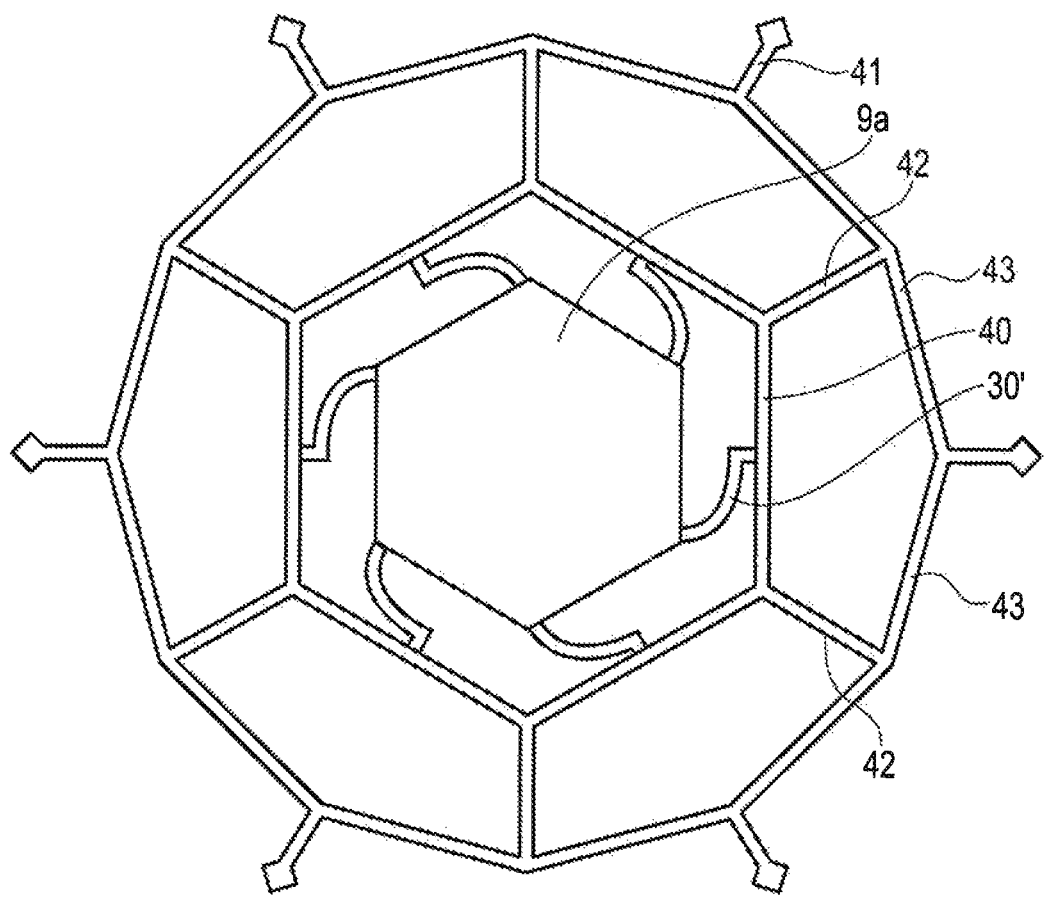
FIG. 25 is a plan view schematically showing a hydrogen sensor according to a fifth embodiment.

FIG. 25 is a plan view schematically showing a hydrogen sensor according to a fifth embodiment.

Each both end parts of a straight member constituting a beam structure 40 is connected to a respective end part of two straight members 42. Both other end parts of the two straight member 42 are connected to both end parts of two straight members 43, respectively. The other end parts of the two straight members 43 are connected to each other. That is, the one straight member, the two straight members 42, and the two straight members 43 of the beam structure 40 constitute a beam structure different from the beam structure 40. Such a beam structure is formed over other straight members constituting the beam structure 40, and as a whole, a beam structure having a cobweb-like (honeycomb-like) shape is constituted. When the beam structure with such a honeycomb-like shape is employed, a more rigid beam structure is realized, and hence it becomes possible to realize the hydrogen sensor having high detection sensitivity.

It should be noted that in the aforementioned embodiments, although the hydrogen sensor has been described, by using absorbing layers configured to absorb other gases in place of the hydrogen occlusion layer, it is possible to implement other types of gas sensors in the same way.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A gas sensor comprising:
a substrate region;
a first electrode provided on the substrate region;
a movable structure provided above the first electrode and including a deformable member configured to deform by absorbing or adsorbing a predetermined gas, a heating member configured to heat the deformable member, and a second electrode; and
a first cavity region provided between the first electrode and the second electrode.

2. The gas sensor of claim 1, further comprising a second cavity region provided in the substrate region and connected to the first cavity region,
wherein
the substrate region includes a semiconductor substrate, and a first insulating layer provided on the semiconductor substrate, and
the second cavity region is provided in the first insulating layer.

3. The gas sensor of claim 2, wherein
a side surface of the first insulating layer defining the second cavity region includes a tapered shape.

4. The gas sensor of claim 2, further comprising a second insulating layer provided on the first insulating layer, and
wherein a through hole is provided in the second insulating layer, and the first cavity region and the second cavity are connected each other via the through hole.

5. The gas sensor of claim 4, wherein the first electrode is fixed on the second insulating layer.

6. The gas sensor of claim 4, wherein a dimension of the second cavity region in a direction from the first electrode toward the movable structure is greater than a dimension of the first cavity region in the direction.

7. The gas sensor of claim 1, further comprising a second cavity region,
wherein the substrate region includes a semiconductor substrate, and the second cavity region is provided in the semiconductor substrate.

8. The gas sensor of claim 1, further comprising a second cavity region,
wherein
the movable structure includes at least one movable section and an electrode section, and
the second cavity is provided below the at least one movable section.

9. The gas sensor of claim 8, wherein
the at least one movable section includes a first movable section and a second movable section, and
the electrode section is provided between the first movable section and the second movable section.

10. The gas sensor of claim 6, wherein
the at least one movable section each includes a deformable member and a heating member, and
the electrode section includes a second electrode and does not include the deformable member.

11. The gas sensor of claim 1, further comprising at least one spring section and a second cavity region provided in the substrate region and connected with the first cavity region, and
wherein
the movable structure includes at least one movable section and an electrode section,
the second cavity is provided below the at least one movable section,
each of the at least one movable section is connected to each of the respective at least one spring section, and
each of the at least one spring section has a thermal resistance that is larger than a sum of a thermal resistance of the first cavity region and a thermal resistance of the second cavity region.

12. The gas sensor of claim 11, wherein
the at least one movable section and the at least one spring section have rotationally symmetric structures when viewed from above.

13. The gas sensor of claim 1, further comprising at least one spring section each having a straight shape, and a second cavity region provided in the substrate region and connected with the first cavity region, and
wherein
the movable structure includes at least one movable section and an electrode section,
the second cavity is provided below the at least one movable section,
each of the at least one movable section is connected to each of the respective at least one spring section, and
each of the at least one spring section has a thermal resistance that is larger than a sum of a thermal resistance of the first cavity region and a thermal resistance of the second cavity region.

14. The gas sensor of claim 1, further comprising at least one spring section each having a tensile stress, and a second cavity region provided in the substrate region and connected with the first cavity region, and
wherein
the movable structure includes at least one movable section and an electrode section,
the second cavity is provided below the at least one movable section,
each of the at least one movable section is connected to each of the respective at least one spring section, and
each of the at least one spring section has a thermal resistance that is larger than a sum of a thermal resistance of the first cavity region and a thermal resistance of the second cavity region.

15. The gas sensor of claim 1, wherein the predetermined gas contains hydrogen.

16. The gas sensor of claim 15, wherein the deformable member contains palladium, an alloy containing palladium, an alloy containing palladium in which supper and silicon are contained, an alloy containing titanium, an alloy containing lanthanum, or metallic glass.

17. The gas sensor of claim 1, wherein the movable structure is configured to move in such a manner that a distance between the first electrode and the second electrode changes accordance to a deformation of the deformable member.

18. A manufacturing method of a gas sensor, comprising:
forming a first insulating layer, a second insulating layer, and a first electrode in sequence on a semiconductor substrate;
forming a third insulating layer on the second insulating layer and the first electrode;
forming a through hole penetrating the third insulating layer and the second insulating layer and reaching the first insulating layer;
forming a fourth insulating layer on the first insulating layer and the third insulating layer to fill the through hole with the fourth insulating layer;

forming a movable structure on the fourth insulating layer, the movable structure including a deformable member configured to deform by absorbing or adsorbing a predetermined gas, a heating member configured to heat the deformable member, and a second electrode; and forming a first cavity region between the first electrode and the second electrode, by removing the fourth insulating layer.

19. The manufacturing method of the gas sensor of claim 18, wherein each of the first and fourth insulating layers contains a first material, and each of second and third insulating layers contain a second material different in type from the first material.

20. The manufacturing method of the gas sensor of claim 19, further comprising forming a second cavity region connected to the first cavity region, by removing a part of the first insulating layer, wherein forming of the first and second cavity region includes etching the first and fourth insulating layers on a condition that etching rates of the first and fourth insulating layers are greater than etching rates of the second and third insulating layers.

* * * * *